United States Patent [19]

Maliga

[11] Patent Number: 5,530,191
[45] Date of Patent: Jun. 25, 1996

[54] METHOD FOR PRODUCING CYTOPLASMIC MALE STERILITY IN PLANTS AND USE THEREOF IN PRODUCTION OF HYBRID SEED

[75] Inventor: Pal Maliga, East Brunswick, N.J.

[73] Assignee: Rutgers, The State University of New Jersey, Piscataway, N.J.

[21] Appl. No.: 217,360

[22] Filed: Mar. 24, 1994

[51] Int. Cl.$^6$ .............................. A01H 5/00; A01H 1/00; C12N 15/05

[52] U.S. Cl. ................... 800/205; 435/172.3; 435/172.1; 47/58; 47/DIG. 1

[58] Field of Search ............................ 47/58; 435/172.3; 800/205

[56] References Cited

U.S. PATENT DOCUMENTS

| | | | |
|---|---|---|---|
| 4,918,006 | 4/1990 | Ellar et al. | 435/69.1 |
| 4,952,496 | 8/1990 | Studier et al. | 435/91 |
| 5,122,457 | 6/1992 | Reim et al. | 435/69.1 |

OTHER PUBLICATIONS

An, Plant Physiol., 81: 86–91 (1986).
Bevan, Nuc. Acids Res., 12: 8711–8721 (1984).
Brent & Ptashne, Cell, 43: 729–736 (1985).
Carey et al., J. Mol. Biol., 209: 423–432 (1989).
Carrer et al., Plant Mol. Biol., 17: 301–303 (1991).
Chen et al., Cell, 50: 1047–1055 (1987).
Cress et al., Science, 251: 87–90 (1991).
Czernylowski et al., DNA, 5: 101–103 (1986).
Deuschele et al., Proc. Natl. Acad. Sci., 86: 5400–5404 (1989).
Dubendorff & Studier, J. Mol. Biol., 219: 45–49 (1991).
Farabaugh, Nature, 274: 765–769 (1978).
Futterer & Hohn, EMBO J., 10: 3887–3896 (1990).
Gatz et al., Proc. Natl. Acad. Scie., 85: 1394–1397 (1988).
Gatz et al., Plant Journal, 2 (3): 397–404 (1992).
Goldberg et al., Plant Cell, 5: 1217–1229 (1993).
Gruissem & Tonkyn Critical Review in Plant Sciences, 12: 19–55 (1993).
Hajdukiewicz et al., Plant Molec. Biol., 0: 1–6 (1994) in print.
Hall et al., Cell, 36: 1057–1065 (1984).
Hanson et al., International Review of Cytology, 94: 213–267 (1985).
Hanson et al., Plant Physiol., 81: 86–91 (1986).
Horsch et al., Science, 227: 1229–1231 (1985).
Jefferson et al., EMBO J., 6: 3901–3907 (1987).
Juranka et al., FASEB, 3: 2583–2592 (1989).
Levings et al., Plant Molec. Biol., 19: 135–147 (1992).
Maliga et al., Phil. Trans R. Soc. Lond. B., 342: 203–208 (1993).
Mariani et al., Nature, 347: 737–741 (1990).

(List continued on next page.)

*Primary Examiner*—Gary Benzion
*Attorney, Agent, or Firm*—Janet E. Reed; Dann, Dorfman, Herrell and Skillman

[57] ABSTRACT

The present invention provides a cytoplasmic male sterility (CMS) system for plants, which is based on modification of the plastid genome. The CMS system comprises three transgenes: a "plastid male sterility" (pms) gene, regulated by a "nuclear male sterility" (rims) gene and a "restorer of male fertility" (rmf) gene. The pms gene is either an inactive gene encoding a toxic gene product or an actively expressed gene encoding an essential gene product. The runs gene is controlled by an anther-specific promoter, and encodes a plastid-directed polypeptide that regulates the pms gene, either by activating expression of the inactive toxic pms gene or by repressing expression of the essential pms gene, which causes plastid and cellular disablement or death in anther tissue, thereby preventing formation of viable pollen. The rmf gene encodes a gene product that prevents the rims gene from regulating the pms gene. Cytoplasmically male-sterile plants are obtained by crossing a parent line containing the pms gene with a parent line containing the nms gene. Male-fertile hybrid seed is obtained from crosses between the cytoplasmically male-sterile plants and a second parent line containing the rmf gene.

49 Claims, 8 Drawing Sheets

OTHER PUBLICATIONS

Mariani et al., Nature, 357: 384–387 (1992).
McLean et al., J. Bacteriol., 169: 1017–1023 (1986).
Ortiz et al., EMBO, 11: (10) 3491–3499 (1992).
Palmer et al., TIG, 6: 115–120 (1990).
Sadowski et al., Nature, 335: 563–564 (1988).
Schnell & Blobel, J. Cell. Biol., 120: 103–115 (1993).
Stern & Gruissem Cell, 51: 1145–1157 (1987).
Studier et al., Methods in Enzymol., 185: 60–89 (1990).
Sugiura, Plant Mol. Biol., 19: 149–168 (1992).
Svab et al., Proc. Natl. Acad. Sci., 90: 913–917 (1993).
Theg et al., Trends in Cell Biol., 3: 186–190 (1993).
Timmermans et al., Jour. Biotech., 14: 333–344 (1990).
Twell et al., Genes and Development, 5: 496–507 (1991).
Ueda and Hayasishi, Ann. Rev. Biochem., 54: 73–100 (1985).
van der Meer et al., Plant Cell, 4: 253–262 (1992).
van Haaren and Ow, Plant Molec. Biol., 23: 525–533 (1993).
Weising et al., Ann. Rev. Genet., 22: 421–477 (1988).
*Methods in Plant Molecular Biology*—A Laboratory Manual Maliga, Klessig, Cashmore, Gruissem, & Varner, eds., Cold Spring Harbor Press (1994, in press; include pages pertinent to pPZP vectors).
Wolfe, Stephen L. (1972) *Biology of the Cell.* Wadsworth Publishing Company, Inc. Belmont California. pp. 154–159.
Frosthoefel et al. (1992) *Discordant inheritance of mitochrondrial and plastid diverse alfalfa genotypes.* Journal of Heredity vol. 83(50. pp. 342–345. BIOSIS abstract BA95:27609.
Poehlman John, Milton. (1987) *Breeding Field Crops.* AVI Publishing Company, Inc. pp. 473–476.

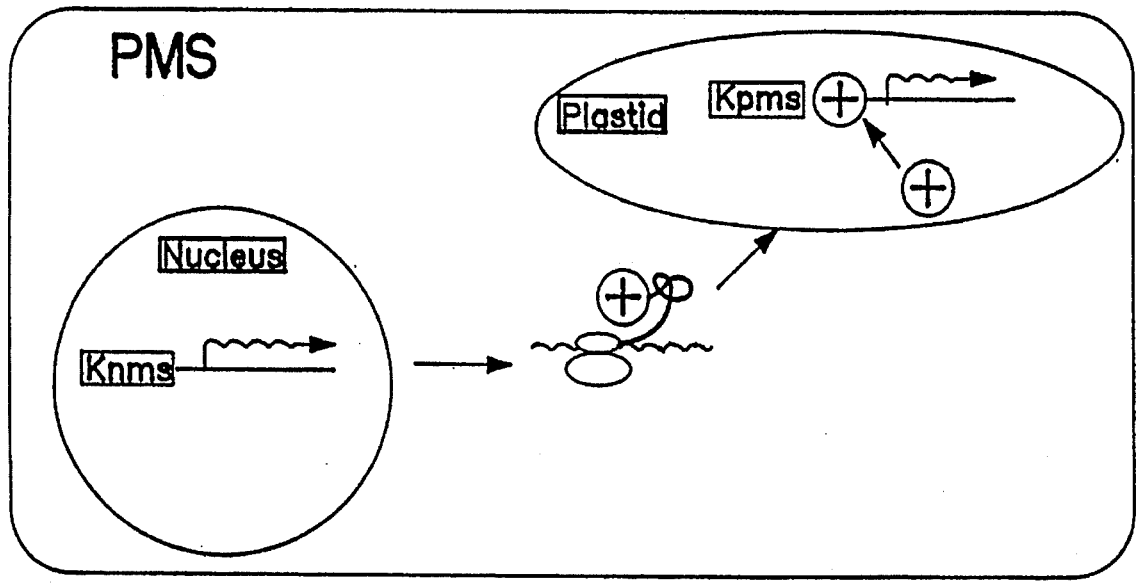
FIG. IA
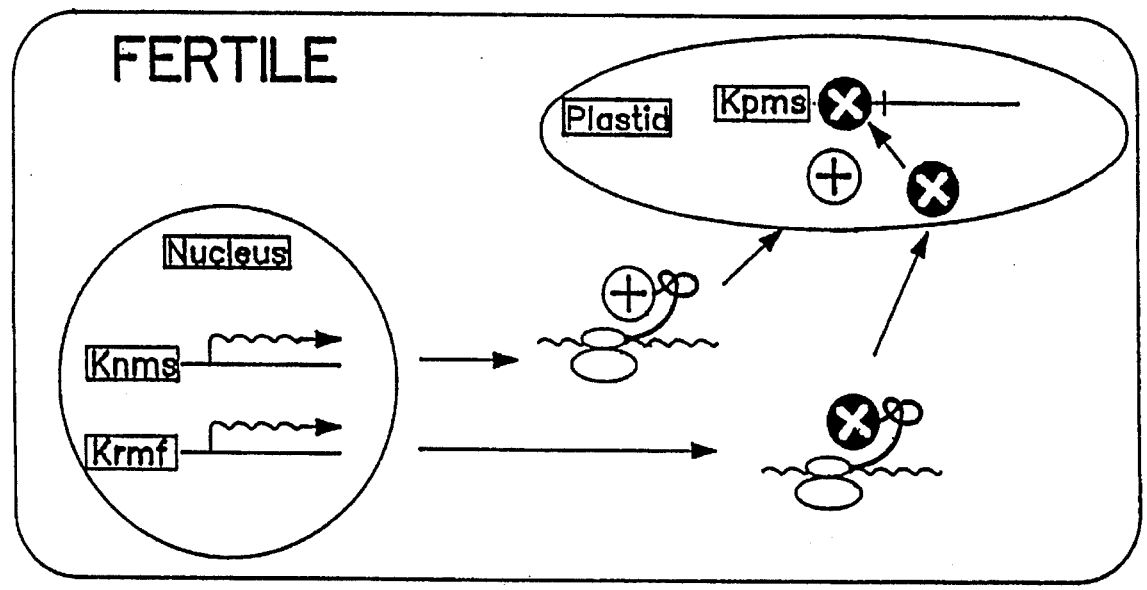
FIG. IB

PT7lac1

```
       EcoRI                                       φ10 promoter        lac operator
      gaattcggGATCTCGATCCCGCGAAATTAATACGACTCACTATAGGGGAATTGTGAGCGG
                         StuI                                        RBS
      ATAACAATTCCCCTCTAGcgaggcctcgCTAGAAATAATTTTGTTTAACTTTAAGAAGGA
            NcoI
      GATATACCATGG
```

PT7lac2

```
       EcoRI                                       φ10 promoter        lac operator
      gaattcggGATCTCGATCCCGCGAAATTAATACGACTCACTATAGGGGAATTGTGAGCGG
                                     RBS        NcoI
      ATAACAATTCCCCTCTAGttcAGTTGTAGGGAGGGATCCATGG
```

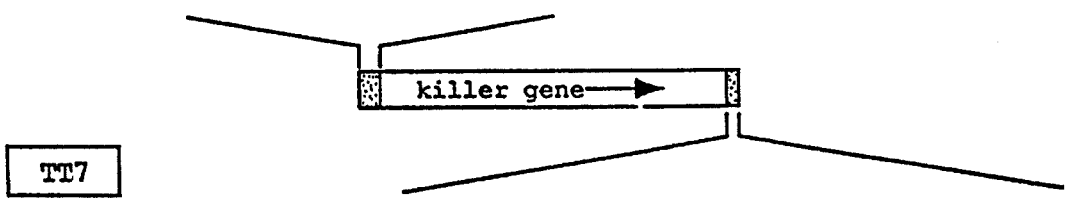

TT7

```
      XbaI                                    T7 terminator
      tctagagcTGAGCAATAACTAGCATAACCCCTTGGGGCCTCTAAACGGGTCTTGAGGGG
                                 HindIII
      TTTTTTGCTGAAAGGAGGAACTATATCCGGcaagctt
```

Trps16T7

```
      XbaI
      tctagaGAAATTCAATTAAGGAAATAAATTAAGGAAATACAAAAAGGGGGGTAGTCATTT

GTATATAACTTTGTATGACTTTTCTCTTCTATTTTTTTGTATTTCCTCCCTTTCCTTTTC

TATTTGTATTTTTTTATCATTGCTTCCATTGAATTaattcatgcaagctcctcgctagag
                                T7 terminator
      cTGAGCAATAACTAGCATAACCCCTTGGGGCCTCTAAACGGGTCTTGAGGGGTTTTTTGC
                HindIII
      TGAAAGGAGGAACTATATCCGGcaagctt
```

FIG. 3

Prrnlac1

102,561                    rrn promoter           -35

GCTCCCCCGCCGTCGTTCAATGAGAATGGATAAGAGGCTCGTGGGA<u>TTGACG</u>TGAGGGGG
              -10           lac operator
CAGGGATGGC<u>TATATTT</u>CT<u>GGAATTGTGAGCGGATAACAATT</u>GGAGCGAACTCCGGGCGA

ATACGAAGCGCTTGGATAC
            102,677

Prrnlac2

102,561                    rrn promoter           -35

GCTCCCCCGCCGTCGTTCAATGAGAATGGATAAGAGGCTCGTGGGA<u>TTGACG</u>AATTGTGA lac operator -10
<u>GCGGATAACA</u><u>TATATTT</u>CTGGGAGCGAACTCCGGGCGAATACGAAGCGCTTGGATAC
                                                                                102,677

PtrnVlac2

102,310                  trnV promoter

GACAATTGAATCCGATTTTGACCATTATTTTCATATCCGTAATAGTGCGAAAAGAAG
                                             -35
GCCCGGCTCCAAGTTGTTCAAGAATAGTGGCG<u>TTGAGT</u>TTCTCGACCCTTTGACT<u>TA</u>
    -10         lac operator
<u>GGATTAGT</u><u>GGAATTGTGAGCGGATAACTATT</u>CAGTTCTATTTCTCGA
                                         102,447

FIG. 7

PrrnlacL1

102,561                    rrn promoter                    -35
    GCTCCCCCGCCGTCGTTCAATGAGAATGGATAAGAGGCTCGTGGGA<u>TTGACG</u>TGAGGGGG
            -10           lac operator
    CAGGGATGGC<u>TATATT</u>TCT<u>GGAATTGTGAGCGGATAACAATT</u>GGAGCGAACTCCGGGCGA
                                          RBS         NcoI
    ATTAGATCTAGAAATAATTTTGTTTAACTTTAAGA<u>AGGAGA</u>TATA<u>CCATGG</u>
102,660             T7 leader PrrnlacL2

102,561                    rrn promoter                    -35
    GCTCCCCCGCCGTCGTTCAATGAGAATGGATAAGAGGCTCGTGGGA<u>TTGACG</u>TGAGGGGG
            -10           lac operator
    CAGGGATGGC<u>TATATT</u>TCT<u>GGAATTGTGAGCGGATAACAATT</u>GGAGCGAACTCCGGGCGA
    EcoRI       RBS     NcoI
    <u>ATTC</u>AGTTGTAG<u>GGAGGG</u>AT<u>CCATGG</u>
102,660     rbcL leader

FIG. 8

METHOD FOR PRODUCING CYTOPLASMIC MALE STERILITY IN PLANTS AND USE THEREOF IN PRODUCTION OF HYBRID SEED

FIELD OF THE INVENTION

This invention relates to the improvement of agronomically and commercially important plants, and specifically to a novel plastid-based transgenic system for the production of cytoplasmically male-sterile plants, and the use of such plants in producing hybrid seed.

BACKGROUND OF THE INVENTION

The discovery that crossing two inbred plant lines yields hybrids with increased productivity has generated great interest among plant breeders in the development of economical methods for the production of hybrid seed. Hybrids generally tend to be more productive, and are more efficient in utilization of nutrients, such as fertilizers and water. $F_1$ hybrids also tend to exhibit superior resistance to environmental stress than parental inbred lines, and can also exhibit desirable disease resistance traits. By producing hybrids of two inbred lines, it may also be possible to combine characteristics that are difficult or impossible to combine in other ways.

Hybrid vigor is a common phenomenon in plants and animals, and has been commercially exploited in plant breeding for many years. Commercial hybrids are presently available for many economically important crop species, and such efforts continue for crops in which hybrids can be produced reliably and economically.

In order to produce hybrid progeny of two inbred lines, cross-pollination must occur. This presents a barrier to hybrid production for many crop plants which are naturally self-pollinating, producing both pollen and egg, often in the same flower. To prevent self-fertilization, the pollen-producing organ must be removed or destroyed in one parent. This may be accomplished by hand-emasculation, i.e., removal of the entire male flower, or removal of anthers from flowers having both functional male and female organs within the same flower. Hand-emasculation is a labor intensive and resultingly expensive process.

Male-sterile parent lines for hybrid seed production may also be produced by the use of chemicals ("gametocides") that prevent formation of viable pollen. These chemicals are also expensive, and are not fully reliable due to limitations in applying the chemicals to the plants.

Uniform cross-pollination may also be accomplished by using genetically male-sterile plants as female parents, planted next to pollen-producing male parents. Using this method, all seed harvested from the row of female parents result from cross-pollination.

Lack of pollen production (i.e., male sterility) in a plant can be due to nuclear mutations or to cytoplasmically-inherited factors. Cytoplasmic male sterility (CMS) is preferred over nuclear-genetic male sterility for the production of hybrid seed because the CMS characteristic is not subject to Mendelian segregation. Hanson & Conde, Int'l. Rev. Cytol., 94: 213–267 (1985). To illustrate, nuclear-genetic male sterility is usually encoded by a single recessive gene, thereby requiring homozygosity for the male-sterile phenotype to be expressed. To propagate nuclear-genetic male sterile plants, the homozygous recessive male steriles must be crossed with an isogenic male-fertile line that is heterozygous for the male sterility gene. Such crosses result in the formation of some percentage of male-fertile plants (50% in a single-gene system), which must be rouged from the field as soon as their fertility can be identified, in order to maintain the effectiveness of the desired male-sterile population. Similar to hand-emasculation, rouging of male-fertile plants from a field is labor intensive and expensive. Thus, segregation of nuclear genes greatly limits the usefulness of nuclear-genetic male sterility for producing hybrid seed.

Nuclear-genetic male sterility suffers from the drawback of Mendelian segregation. By contrast, cytoplasmic male sterility is expressed in all offspring of a hybrid cross between a CMS inbred and a male-fertile parent. It is for this reason that the CMS characteristic is the preferred method for production of hybrid seed.

Naturally-occurring cytoplasmic male sterility is attributable to mutations in the mitochondrial genome. The relationships between these mitochondrial mutations and cytoplasmic male sterility is variable from species to species, and is not well understood. In maize, one of the best-characterized mitochondrial CMS systems, cytoplasmic male sterility in the Texas cytoplasm (CMS-T) appears to be associated with the expression of a 13-kD polypeptide. Hansen, Ann. Rev. Genet., 25:461–486 (1991); Levings & Siedow, Plant Molec. Biol., 19: 135–147 (1992). It was shown that this polypeptide is a transmembrane protein that increases the permeability of cell membranes. The polypeptide has no obvious detrimental effect in normally-dividing vegetative cells, but by an as yet unknown mechanism, causes excessive permeability of tapetal cell membranes and consequent disruption of pollen formation. Production of the 13 kD polypeptide has been correlated with susceptibility of CMS-T maize to plant pathogens such as *Bipolaris maydis* and *Phyllosticta maydis*.

In plant breeding programs where naturally-occurring CMS cytoplasm is available, seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a fertile inbred with normal cytoplasm, carrying a fertility restoring gene ("restorer" line, which need not be isogenic with the CMS line). The CMS line is propagated by pollination with the maintainer line. All plants from this cross will be male-sterile since the CMS cytoplasm is derived from the female parent. Hybrid seed is produced by pollination with a second inbred line carrying fertility restorer (Rf) gene. If no restorer gene is available, sterile hybrids still can be obtained by pollination with a different inbred that does not carry a fertility restorer gene. Such hybrids are useful for crops in which the vegetative tissue is utilized (e.g., tobacco leaf or petunia flowers). However, in most crops, the seeds are the valuable portion of the crop, so fertility of the hybrids in these crops must be restored.

Although cytoplasmic male sterility is useful for hybrid seed production, its usefulness is often limited by the numerous practical problems associated with naturally-occurring cytoplasmic male sterility. These include the inability to identify CMS cytoplasms or nuclear restorer alleles, as well as assorted undesirable traits such as disease sensitivity (as described above), reduced fertility, and the like. Each of these difficulties arises from the lack of understanding of the mitochondrial mechanism for cytoplasmic male sterility and restoration of fertility. Clearly, the value of cytoplasmic male sterility would be greatly increased if a CMS system were developed whose components were fully understood and characterized, and which could be confidently manipulated without the risk of detrimental side effects.

SUMMARY OF THE INVENTION

The present invention provides a novel CMS system based on modification of the plastid genome instead of the mitochondrial genome, and employing three transgenes: a plastid male sterility gene and two nuclear genes that regulate the expression of the plastid male sterility gene.

According to one aspect of the present invention, a method is provided for producing cytoplasmically male-sterile plants. First, a parent plant line is selected. A plastid-transgenic parent plant is produced by stably transforming plastids in cells of the parent line with a plastid male sterility gene, pms, and regenerating a plant. The pms gene is capable of regulation by a nuclear-encoded plastid-directed regulator polypeptide. When that regulation occurs in anther tissue, formation of viable pollen is disrupted. In one embodiment, referred to herein as the "pollen-kill" method, the pms gene is an inactive gene, comprising a coding region that encodes a substance capable of disabling or killing plastids, thereby disrupting formation of viable pollen, operably linked to target nucleotide sequence for activating gene expression. In another embodiment, referred to herein as the "pollen-starve" method, the pms gene comprises an essential gene of the plastid genome, operably linked to target nucleotide sequence for preventing gene expression. This gene replaces the native plastid gene, and preventing expression of the gene causes damage or death of plastids, thereby disrupting formation of viable pollen. Plastid-transgenic plants containing the pms gene are fertile. Next, different cells of the parent plant line are subjected to stable nuclear transformation with a nuclear male sterility gene, nms, which comprises an anther-specific 5' regulatory nucleotide sequence operably linked to a coding nucleotide sequence that encodes the aforementioned plastid-directed "regulator" polypeptide capable of entering plastids and regulating the pms gene by interacting with the target nucleotide sequence, either by activation of expression ("pollen-kill" method) or preventing expression ("pollen-starve" method). A plant is regenerated from the nuclear-transformed parent plant cells. Such plants are also fertile. Cytoplasmically male-sterile plants are produced by crossing the plastid-transgenic parent plant with the nuclear-transgenic parent plant, thereby providing the complete system for anther-specific plastid disablement or death, which disrupts formation of viable pollen.

According to another aspect of the present invention, a method is provided for producing male-fertile hybrid seed from two parent plant lines, one of which comprises the cytoplasmically male-sterile plant line described above. According to this method, cytoplasmically male-sterile parent plants are produced as described above. A second parental plant line is then selected. From this line a male fertility-restoring parent plant is produced by subjecting cells of the second parent plant line to stable nuclear transformation with a "restoration of male fertility" (rmf) gene. The rmf gene comprises a nucleotide sequence that encodes a "restorer" gene product capable of interfering with the nms gene, either by blocking expression of the nms gene itself, or by blocking expression of an activatable toxic pms gene. A plant is regenerated from the stably nuclear-transformed cells. The cytoplasmically male-sterile line is then crossed with the fertility-restoring line, whereupon expression of the rmf gene prevents the aforesaid regulation of the pms gene by the regulator polypeptide, thereby restoring male fertility to the hybrid plants.

According to other aspects of the present invention, DNA constructs and transgenic plants are provided for practice of the invention. A nuclear-transgenic plant comprising the nms gene, and a plastid-transgenic plant from the same parental line, comprising the pms gene, are provided. A cytoplasmically male-sterile plant, produced by crossing the nuclear-transgenic plant with the plastid-transgenic plant is also provided. A nuclear-transgenic plant of a second parental plant line is provided, which comprises the rmf gene. Male-fertile hybrid plants are also provided, which are produced by crossing the cytoplasmically male-sterile parental plant with the second parental plant line containing the rmf gene.

BRIEF DESCRIPTION OF THE DRAWINGS

FIGS. 1A and 1B: Schematic diagram of a preferred embodiment of the "pollen-kill" method of plastid male sterility (PMS) employing the T7 RNA polymerase/lac repressor system. (FIG. 1A): Expression of male sterility genes in the taperum cells or microspores of sterile plants. The nuclear nms gene ("Knms") is transcribed, the encoded polypeptide (T7 RNA polymerase) is translated on cytoplasmic ribosomes and is imported into plastids. Subsequent transcription of the plastid killer gene ("Kpms") from the T7lac promoter causes cellular death ("+" symbolizes the positive regulator, T7 RNA polymerase, which is specific for the T7 promoter). (FIG. 1B): Expression of male sterility genes in the tapetum cells or microspores of fertile hybrid plants. The lac repressor, the product of the nuclear fertility restorer gene (Krmf) binds to the Kpms T7/lac promoter in plastids thus preventing transcription of the toxic gene by the Knms gene product. (White "X" in black circle symbolizes specific binding of lac repressor to the lac operator on the T7/lac regulatory sequence).

(FIG. 2A): Expression of male sterility genes in the tapetum cells or microspores of sterile plants. The nuclear rims gene ("Snms") is transcribed and the encoded lac repressor is imported into plastids where it blocks the expression of an essential gene (Spms) whose promoter contains a lac repressor binding site. Lack of expression of the essential Spms gene causes cellular death (white "X" in black circle symbolizes specific binding of the lac repressor to the lac operator sequence of the Spms gene). (FIG. 2B): Expression of male sterility genes in the tapetum cells of fertile hybrid plants. The fertility restorer gene (Srmf) encodes a nuclear-targeted repressor that prevents a transcription of the nuclear Snms gene, by way of a repressor binding site engineered on the Snms gene, thereby enabling expression of the Spms genes (white "-" in black circle symbolizes specific binding of the nuclear-targeted repressor to its repressor binding site on the Snms gene).

FIG. 3. Cassettes for the expression of the Kpms in plastids, for the "pollen-kill" method. The DNA sequences are shown for the PTlac1 (Sequence I.D. No. 1) and PT7lac2 (Sequence I.D. No. 2) promoters and the TT7 (Sequence I.D. No. 3) and Trps16T7 (Sequence I.D. No. 4) transcription terminators. RBS stands for ribosome binding site, the T7 phage gene 10 (φ10) promoter, the lac operator and the relevant restriction sites are underlined. The translational initiation codon included in the NcoI recognition sequence is in bold type.

FIG. 7. Modified promoter sequences used to transcribe Spms genes for the "pollen starve" method. The Prrnlac1 (Sequence I.D. No. 13) and Prrnlac2 (Sequence I.D. No. 14) promoters are derived from the rRNA operon promoter, the PtrnVlac2 (Sequence I.D. No. 15) promoter is derived from the trnV gene. Note underlined −10 and −35 promoter elements and the lac operator sequence (bold). Numbers indicate the position of the nucleotide in the tobacco plastid genome (Shinozaki et al., EMBO J., [: 2043-2049, 1986).

FIG. 8. Modified promoter sequence used to express protein-coding Spms genes for the "pollen starve" method. The promoters shown are derivatives of the rRNA operon promoter, and have the leader sequence of either the T7 phage gene 10 leader (PrrnlacL1; Sequence I.D. No. 16) or the plastid rbcL gene leader (PrrnlacL2; Sequence I.D. No. 17). Note underlined −10 and −35 promoter elements and the lac operator sequence (bold). Numbers indicate the position of the nucleotide in the tobacco plastid genome (Shinozaki et al., 1986, supra).

DETAILED DESCRIPTION OF THE INVENTION

Figure 2A:
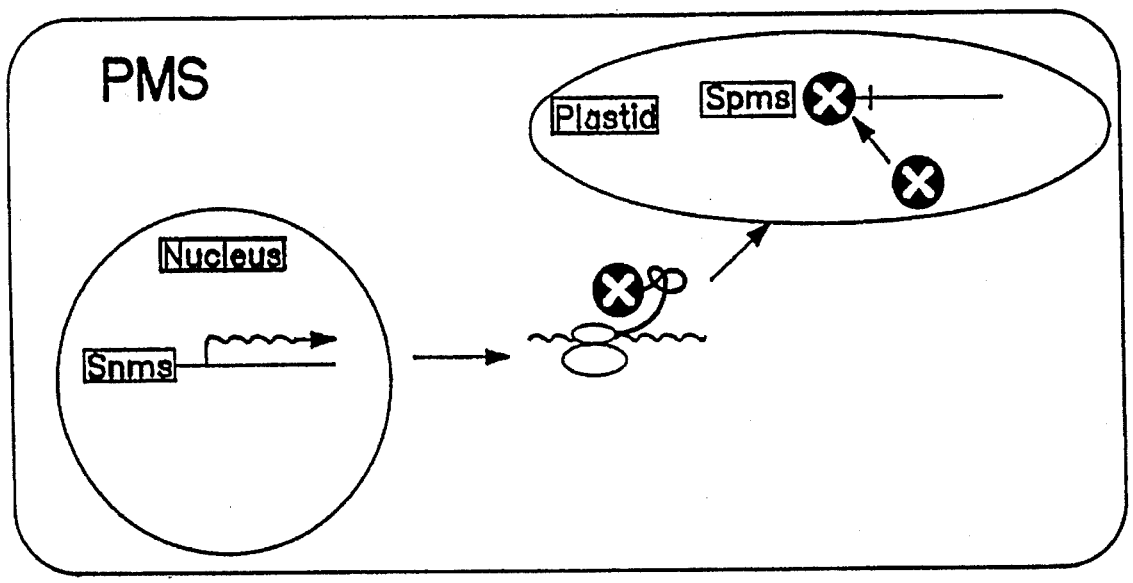
FIGS. 2A and 2B: Schematic diagram of a preferred embodiment of the "pollen-starve" method of plastid male sterility employing a plastid-directed lac repressor and a nuclear-directed tet repressor.
Figure 2B:
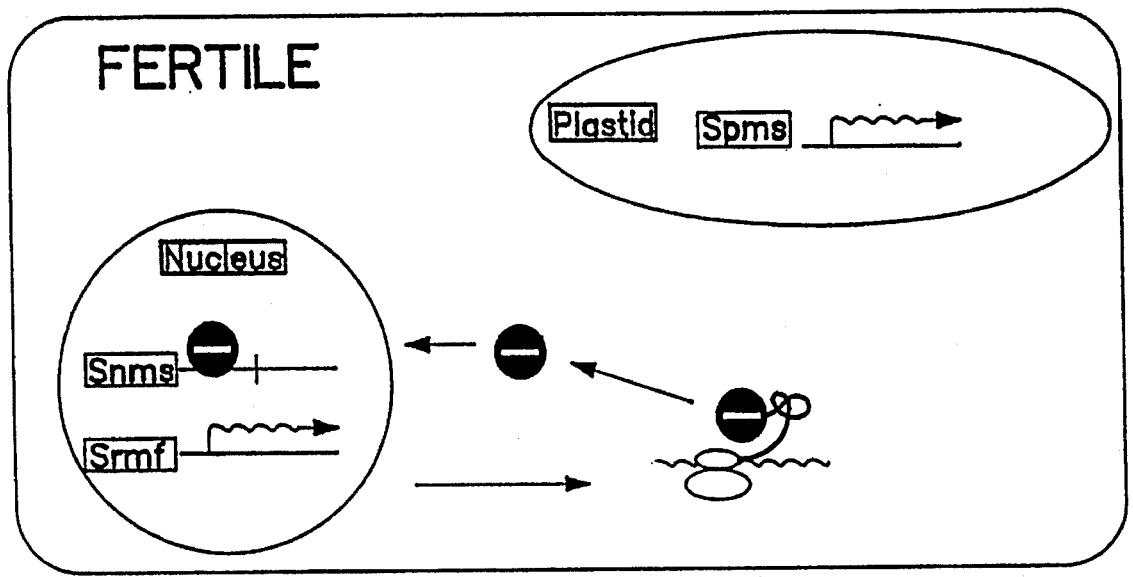

The transgenic CMS system of the present invention is based on the tenet that viable, functional chloroplasts in developing anther tissue (particularly the taperum or microspores) are essential for formation of viable pollen. The three-transgene system comprises a plastid male sterility (pms) gene that is regulated by two nuclear genes. One of the two nuclear regulatory genes is a nuclear male sterility (rims) gene designed to be expressed only in anther tissue. The nms gene encodes a plastid-directed polypeptide that regulates the pms gene, either by activation or inactivation of the pms gene, which causes the transformed plastids of the selected anther tissue to be disabled or to die, thereby preventing formation of viable pollen. The other nuclear gene, the restorer of male fertility (rmf) gene, encodes a gene product that prevents the nms gene from regulating the pms gene.

The detailed description set forth in sections I–III below describes preferred methods for making and using the DNA constructs and transgenic plants of the present invention and for practicing the methods of the invention. Section I sets forth general methods for constructing the plastid-based CMS systems of the invention (sometimes referred to herein as "plastid male sterility" or "pms" systems). Sections II and III set forth two preferred embodiments of the plastid-transgenic CMS system, the "pollen-kill" method and the "pollen starve" method, and described DNA constructs and other components useful for practicing each of the two preferred embodiments. Any molecular cloning or recombinant DNA techniques not specifically described are carried out by standard methods, as generally set forth, for example, in Sambrook et al., "DNA Cloning, A Laboratory Manual," Cold Spring Harbor Laboratory, 1989.

I. GENERAL METHODS FOR CONSTRUCTING PLASTID-TRANSGENIC CMS SYSTEMS AND FOR PRODUCTION OF HYBRID SEED

The transgenic CMS systems of the invention are prepared and used according to the general methods set forth below for nuclear and plastid transformation of higher plants, maintenance of parental plant lines and production of hybrid seed.

A. DNA Constructs and Methods for Stably Transforming Plastids With a pms Gene and Regenerating Plastid-Transgenic Plants Methods and DNA constructs for stable, high-efficiency transformation of plastids and expression of recombinant proteins in plastids are known in the art. The methods and constructs described in the following references are preferred for practice of the present invention: Svab et al., Proc. Natl. Acad. Sci. USA, 87:8526–30 (1990); Svab & Maliga, Proc. Natl. Acad. Sci. USA, 90: 913–17 (1993); Carrer et al., Mol. Gen. Genet., 241:49–56 (1993); Staub & Maliga, EMBO J., 12: 601–06 (1993); and U.S. patent application Ser. Nos. 08/111,398 and 08/189,256; all the aforementioned disclosures describe the state of the art with respect to stable, high-efficiency plastid transformation and expression of recombinant genes in plastids.

The following definitions will facilitate the understanding of the plastid transformation methods used in accordance with the present invention:

Heteroplasmic: refers to the presence of a mixed population of different plastid genomes within a single plastid or in a population of plastids contained in plant cells or tissues.

Homoplasmic: refers to a pure population of plastid genomes, either within a plastid or within cells and tissues.

Transformation of plastids: stable integration of transforming DNA into the plastid genome that is transmitted to the seed progeny of plants containing the transformed plastids.

The aforementioned preferred methods and constructs for plastid transformation rely on the use of a non-lethal selection means, which imparts a selectable phenotype to cells containing transformed plastids. The terms "selective marker" or "selectable marker" refer to a phenotype that identifies a successfully transformed organelle, cell or tissue, when a gene or allele encoding the selective marker is included in the foreign DNA used for transformation. Commonly used selective markers include resistance to antibiotics, herbicides or other compounds, which would be lethal to cells, organelles or tissues not expressing the resistance gene or allele. Selection of transformants is accomplished by growing the cells or tissues under selective pressure, i.e., on media containing the antibiotic, herbicide or other compound. If the selective marker is a "lethal" selective marker, cells which express the selective marker will live, while cells lacking the selective marker will die. If the selective marker is "non-lethal", transformants (i.e., cells expressing the selective marker) will be identifiable by some means from non-transformants, but both transformants and non-transformants will live in the presence of the selection pressure.

A selective marker may be non-lethal at the cellular level, but selective at the organellar level; such is the case for the selective marker preferred herein for plastid transformation. For example, the antibiotic spectinomycin inhibits translation in plastids, but not in the cytoplasm. Plastids sensitive to spectinomycin are incapable of producing proteins comprising the photosynthetic apparatus. In the presence of spectinomycin, cells comprising such plastids are kept alive by growing them under photoheterotrophic conditions (i.e., supplying an exogenous carbon source), but the plastids therein grow more slowly, and the cells or tissues are bleached white, instead of being green. In contrast, plastids expressing the selective phenotype of spectinomycin resistance multiply at a faster rate and the cells containing such plastids are green. In a mixed population of cells containing transformed and non-transformed plastids, the sensitive non-transformants will be vastly outnumbered and will be diluted out during the course of plastid/cell division under selection pressure, and essentially only transformed plastids will comprise the plastid population (homoplasmic cells or tissues, as defined above). Thus, a non-lethal selective marker refers to non-lethality at the cellular level, wherein sensitive cells or tissues can be grown in the selective medium, but resistant tissues are readily identifiable therefrom.

Plastid transformation requires: (1) a method for delivering the DNA through the double membrane of the plastid; (2) integration of the heterologous DNA without interfering with the normal function of the plastid genome (accomplished either by replacement of an existing plastid gene or inserting additional genes at appropriate locations in the plastid genome); and (3) efficient selection for the transformed plastid genome, preferably through the use of a dominant-type non-lethal selectable marker, as described by Svab & Maliga, 1993, supra (describing the aadA gene as a selectable marker gene for high-efficiency transformation of tobacco chloroplasts).

Several methods are available to introduce DNA into the plastids of flowering plants, including, but not limited to, Agrobacterium vectors, polyethylene glycol (PEG) treatment of protoplasts, bombardment of cells or tissues with microprojectiles coated with the plastid-transforming DNA (sometimes referred to herein as "biolistic DNA delivery") and temporary holes cut by a UV laser microbeam. Other methods include use of geminivirus vectors, calcium phosphate treatment of protoplasts, electroporation of isolated protoplasts and agitation of cell suspensions with microbeads coated with the transforming DNA. The biolistic method, as described by Svab & Maliga, 1993, supra is preferred for plastid transformation because it can be used on a wide variety of plants and tissues therein, including species or genera not amenable to cell or protoplast culture or regeneration. In an alternative embodiment, useful in plant systems where protoplasts may be obtained and regenerated into intact plants, plastid transformation may be achieved by polyethylene glycol (PEG) treatment of protoplasts in the presence of the transforming DNA. Methods for stable plastid transformation in PEG-treated protoplasts are exemplified in tobacco by Golds et al., Bio/Technology, 11: 95–97 (1993).

DNA constructs useful for stable plastid transformation with the pms gene (sometimes referred to herein either as "transforming DNA" or "insertion vectors") comprise the following elements: (1) a DNA sequence homologous to a region of the plastid genome being transformed (sometimes referred to herein as a "targeting segment" or "targeting fragment") of sufficient length to ensure the homologous recombination event necessary for incorporation of the transforming DNA into the plastid genome, (2) a non-lethal selectable marker gene, such as the aadA gene, and (3) the pms gene, both genes operably linked to respective 5' and 3' regulatory regions for expression in plastids. Such vectors are conveniently assembled as chimeric genes, wherein each coding region (i.e., the coding region for the selectable marker gene and the coding region for the pms gene) is flanked by the appropriate 5' and 3' regulatory sequences. The 5' and 3' regulatory segments for the selectable marker coding segment are chosen such that the selectable marker gene is effectively expressed, thereby conferring the non-lethal selectable phenotype. The pms gene 5' and 3' regulatory segment are selected as described above, such that the gene is capable of being activated and inactivated under control of the nuclear nms and rmf genes. Such chimeric genes are flanked on both sides by portions of the targeting segment.

The targeting segment of an insertion vector should be sufficiently large to ensure homologous recombination between the transforming DNA and the plastid genome. To accomplish this, the targeting segment should be at least about 50 bases long, and preferably between 500 and 1,500 bases on each side of the DNA to be inserted into the plastid genome.

The targeting segment is selected such that the transforming DNA does not disrupt the expression of adjacent plastid genes. Useful targeting segments may be identified by one skilled in the art, due to the availability of extensive genome mapping information and sequence information for several plastid genomes, combined with applicability of this information to other plastid genomes as a result of the high degree of conservation among plastid genomes (Palmer, Trends in Genetics, 6: 115–120, 1990; Sugiura, Plant Mol. Biol., 19: 149–168, 1992).

For the "pollen-starve" method of the present invention, the targeting segment comprises the gene to be replaced, and completely replaces that gene without disturbing adjacent genes on the plastid genome. Replacement is accomplished by linking the selectable marker gene downstream from the replacement plastid gene, and selecting transformants displaying the selectable phenotype (see Maliga et al., Phil. Trans. R. Soc. Lond. B, 342: 203–208 (1993)).

For the "pollen-kill" method, a targeting segment is selected such that the transforming DNA is inserted into the plastid genome at a transcriptionally silent location, without disrupting plastid genes. Given that the 3' regions of plastid genes terminate transcription inefficiently (Gruissem & Tonkyn, Critical Review in Plant Sciences, 12: 19–55, 1993), some degree of read-through transcription might be expected when inserting the transforming DNA at almost any location in the plastid genome. An insertion site in the inverted repeat region, between the trnV gene and the rps12/7 operon, is particularly useful in view of this fact, because the transforming DNA is transcribed without significant read-through transcription when oriented toward the rps12/7 operon. This lack of read-through transcription in the trnVrps- 12/7 insertion site is likely due to the fact that the flanking plastid genes or operons are divergently transcribed (i.e., transcribed from opposing strands, in opposite directions). Hence, targeting segments directed to sites between other divergently transcribed genes may also be useful in the practice of the present invention. These include, but are not limited to, sites between trnL and ORF2280 in the inverted repeat region, and between trnS and ORF168 and trnW and petG in the large single-copy region. Alternatively, insertion sites between any two tRNA genes may also be useful, since tRNA genes are relatively efficient terminators of transcription (Stern & Gruissem, Cell, 51: 1145–57, 1987). The same result may also be achieved by flanking the insertion sites with transcription terminators which can be synthesized or excised from source genes and cloned.

The selectable marker gene and pms gene may be provided in expression cassettes for insertion into the targeting segment. An expression cassette, as used herein, comprises 5' and 3' regulatory segments, preferably adapted for convenient mixing and matching by standard recombinant DNA techniques. Expression cassettes are used to produce chimeric pms genes and selectable marker genes for assembly of insertion vectors. Insertion vectors for transforming plastids with the pms gene thus contain at least one other gene, which confers a non-lethal selectable phenotype.

Expression cassettes comprise 5' and 3' regulatory segments to control expression of the various coding segments. The 5' regulatory segment controls the amount and specificity of expression in plastids. The 3' regulatory segment confers mRNA stability. The 5' and 3' regulatory segments are preferably derived from 5' and 3' regulatory regions of endogenous plastid genes, which may be further modified. Other 5' and 3' regulatory regions may also be used, particularly such regions taken from E. coli, cyanobacteria, photosynthetic bacteria, bacteriophages and plant viruses.

To obtain high levels of protein expression of the selectable marker gene and the essential pms gene in anther plastids, modified non-photosynthetic promoters may be utilized in the 5' regulatory segment. A strong promoter of this class is the 16S ribosomal RNA operon promoter, Prrn, described by Svab & Maliga, 1993, supra.

In addition to having promoter elements for directing transcription, 5' regulatory segments may contain additional expression-promoting elements for regulating translation, such as ribosome binding sites contained in 5' untranslated regions (UTRs) of plastid genes, as well as sequences encoding a few of the N-terminal amino acids of the plastid gene.

An example of a rrn operon promoter that has been engineered for expression of the spectinomycin resistance gene, aadA, is disclosed by Svab & Maliga, 1993, supra. This 5' regulatory segment contains a segment of the rrn operon 5'-region, including the −10 and −35 promoter elements, fused with 18 nucleotides of the highly-expressed rbcL untranslated region, which includes the GGGUGGG ribosome binding site. This 5' regulatory segment was capable of directing constitutive expression of the uidA gene in transformed plastids. As another example, the same promoter described by Carrer et al., 1993, supra, was capable of directing expression of the kan gene.

It has also been found that expression can be improved by including in the 5' regulatory segment the entire rbcL leader sequence from −16 to +18 relative to the translation start site. Given the importance of mRNA leader sequences (i.e., 5' UTRs and N-terminal coding regions) for high level protein expression, other useful leader sequences may be derived from other highly expressed genes, particularly highly expressed viral genes (e.g., the omega sequence of tobacco mosaic virus (TMV) coat protein, untranslated leaders from alfalfa mosaic virus (AMV) RNA4 or brome mosiac virus (BMV) RNA3, and the phage T7 leader sequence (see FIG. 8 and Example 4).

An example of 3' regulatory segments suitable for practice of the present invention is disclosed by Staub & Maliga, 1993, supra, and also in Example 1 (FIG. 3). These segments are derived from the 3' untranslated regions of various plastid genes and the T7 phage gene 10.

Using the constructs described hereinabove, stably plastid-transformed multicellular plants comprising the pms gene may be obtained as follows:

(1) provide the pms gene in an insertion vector comprising a non-lethal selectable marker gene and an appropriate targeting segment;

(2) deliver the transforming DNA into the plastid (preferably by the biolistic method), thereby enabling integration of the transforming DNA without interfering with the normal function of the plastid genome;

(3) maintain the treated cells or tissues on the appropriate selection medium and repeat sub-cloning until homoplasmic cells or tissues are obtained;

(4) identify homoplasmic cells or tissues by their expression of the selectable phenotype; and (5) grow the identified transformants to mature plants and evaluate their progeny for maintenance of the selectable phenotype and presence of the pms gene.

B. Methods for Obtaining Nuclear-Transgenic Plants Comprising the nms Gene or the rmf Gene Transformation of plant nuclei may be accomplished according to the same methods as those described for plastid transformation. These include, but are not limited to, Agrobacterium vectors, PEG treatment of protoplasts, biolistic DNA delivery, UV laser microbeam, gemini virus vectors, calcium phosphate treatment of protoplasts, electroporation of isolated protoplasts, agitation of cell suspensions with microbeads coated with the transforming DNA, direct DNA uptake, liposome-mediated DNA uptake, and the like. Such methods have been published in the art. See, e.g., *Methods for Plant Molecular Biology*, Weissbach & Weissbach eds., Academic Press, Inc. (1988); *Methods in Plant Molecular Biology*, Schuler & Zielinski, eds., Academic Press, Inc. (1989); *Plant Molecular Biology Manual*, Gelvin Schilperoort, Verma, eds., Kluwer Academic Publishers, Dordrecht (1993); and *Methods in Plant Molecular Biology—A Laboratory Manual*, Maliga, Klessig, Cashmore, Gruissem & Varner, eds., Cold Spring Harbor Press (1994, in press).

The method of transformation depends upon the plant to be transformed. The biolistic DNA delivery method has already been described for transformation of plastids and can also be used for nuclear transformation. In another embodiment of the invention, Agrobacterium vectors are used to advantage for efficient transformation of plant nuclei.

In a preferred embodiment, the rims gene (as well as the rmf gene described below) is introduced into plant nuclei in Agrobacterium binary vectors. Such vectors include, but are not limited to, BIN19 (Bevan, Nucl. Acids Res., 12: 8711–8721, 1984) and derivatives thereof, the pBI vector series (Jefferson et al., EMBO J., 6: 3901–3907, 1987), and binary vectors pGA482 and pGA492 (An, Plant Physiol., 81: 86–91, 1986). A new series of Agrobacterium binary vectors, the pPZP family, is preferred for practice of the present invention. The use of this vector family for plant transformation is described by Svab et al. in *Methods in Plant Molecular Biology—A Laboratory Manual*, Maliga, Klessig, Cashmore, Gruissem and Varner, eds., Cold Spring Harbor Press (1994, in press).

Using an Agrobacterium binary vector system for transformation, the nms or rmf gene is linked to a nuclear drug resistance marker, such as kanamycin or gentamycin resistance. The nms gene and the rmf gene are preferably linked to two different drug resistance markers, so that the two genes can be selected independently from one another. Agrobacterium-mediated transformation of plant nuclei is accomplished according to the following procedure:

(1) the nms gene or rmf gene is inserted into the selected Agrobacterium binary vector;

(2) transformation is accomplished by cocultivation of plant tissue (e.g., leaf discs) with a suspension of recombinant Agrobacterium, followed by incubation (e.g., two days) on growth medium in the absence of the drug used as the selective medium (see, e.g., Horsch et al., Science 227: 1229–1231, 1985);

(3) plant tissue is then transferred onto the selective medium to identify transformed tissue; and (4) identified transformants are regenerated to intact plants.

It should be recognized that the amount of expression, as well as the tissue specificity of expression of the nms or rmf genes in transformed plants will likely vary depending on the position of their insertion into the nuclear genome. Such position effects are well known in the art; see Weising et al., Ann. Rev. Genet., 22:421–477 (1988). For this reason, several nuclear transformants should be regenerated and tested in crosses with the plastid-transformed $A^P$ line (or an $A^P$ "test" line wherein the pms gene is a reporter gene such as uidA, encoding β-glucuronidase (GUS)) to identify transformants expressing the nuclear transgene appropriately.

C. Preparation and Maintenance of Parental Lines and Production of Hybrid Seed In accordance with the methods described above, the three transgenes are introduced into selected plant lines as follows. A parent line, parent A, is selected. Plastids of a parent A plant are stably transformed with the pms gene, and a plastid-transgenic plant ($A^P$) is regenerated. Nuclei of another parent A plant are stably transformed with the nms gene, and a nuclear-transgenic plant ($A^N$) is regenerated. A second parent line, Parent B, is selected. Nuclei of the parent B line are stably transformed with the rmf gene, and a nuclear-transgenic plant ($B^R$) is regenerated.

Having produced the parental lines, $A^P$, $A^N$, and $B^R$, seed propagation and hybrid seed production may be easily accomplished. All nuclear-transformed parental lines are inbred to homozygosity. The plastid-transformed $A^P$ line is homoplasmic. All parental lines are male fertile and can be maintained indefinitely. To obtain cytoplasmically male-sterile progeny, $A^N$ (pollen parent) is crossed with $A^P$ (female parent), using various techniques (such as removing the male portions of $A^P$ and using $A^N$ as the male parent) to ensure that crossed, rather than selfed, seed is obtained. These progeny are male-sterile because they have both the pms gene and the nms regulatory gene, which leads to disablement or death of plastids or cells in the selected anther tissue and subsequent failure to form viable pollen. A stable $A^S$ line is obtained by repeated back-crosses with $A^N$, which yields homozygotes for $A^N$ in the $A^P$ cytoplasm.

Seeds of male-sterile $A^S$ plants may be propagated by back-crossing $A^S$ plants with the nuclear-transformed parent, $A^N$. For propagation of $A^S$ seed, $A^S$ plants may be planted next to $A^N$ plants in alternating rows, and seeds harvested separately by row. Plants grown from seed of the $A^S$ row will be male sterile. Because male sterility is generated at the plastid level via transgenic plastids, the male sterility trait is uniformly inherited cytoplasmically without production of unwanted male fertiles due to segregation of nuclear genes.

The second parent line, parent B is used for production of hybrid seed. If male-fertile hybrid plants are not necessary, a simple cross of $A^S \times B$ is made, and the $A^SB$ progeny will inherit the CMS trait to produce plants that are also male-sterile, since progeny will carry at least one copy of the nms gene, but no rmf gene. If, on the other hand, the hybrid seeds are desired to grow into male fertile plants, the nuclear-transgenic parent, $B^R$, is employed. For production of male-fertile hybrid seed, $A^S$ plants may be planted next to the pollen-forming $B^R$ plants. Since the $A^S$ plants do not have fertile pollen, all seed produced by $A^S$ plants are the results of fertilization with $B^R$ pollen. Crosses of $A^S$ with $B^R$ result in the formation of hybrid $A^SB^R$ seeds that will grow into male-fertile plants, due to expression of the rmf gene, which blocks the regulatory activity of the nms gene product on the pms gene.

II. THE "POLLEN-KILL" METHOD

In one embodiment of the invention, referred to herein as the "pollen-kill" method, the pms gene is an inactive gene modified so that it can be activated and, optionally, inactivated. When activated, the pms gene expresses a gene product that is toxic or lethal to plastids. The nms gene is an anther-specific nuclear gene that encodes a plastid-directed activator polypeptide capable of entering plastids and activating the toxic pms gene, thereby disabling or killing the plastids of the selected anther tissue. The rmf gene of the B parent encodes a "restorer" gene product capable of interfering with the action of the activator polypeptide, thereby preventing formation of the lethal pms gene product. In a preferred embodiment, the rmf gene encodes a plastid-directed polypeptide capable of entering plastids and interfering with the activator polypeptide there (e.g., by interacting with the inactivation site of the pms gene, thereby overriding the effect of the activator polypeptide). In another embodiment, the rmf gene encodes a cytoplasmic gene product that interferes with the activator precursor polypeptide before it enters the plastid (e.g., is targeted to the nucleus and inhibits expression of the nms gene).

The "pollen-kill" method is exemplified by a system utilizing T7 RNA polymerase as the activator polypeptide, a lac repressor as the restorer polypeptide and a plastid-toxic "killer" gene operably linked to a T7/lac promoter. In this embodiment, the nms gene product comprises the highly specific T7 bacteriophage RNA polymerase fused to a plastid transit peptide (e.g., that of the RuBisCO small subunit) to direct the polymerase into the plastid stromal compartment. The T7 RNA polymerase is a comparatively simple polymerase, comprising a monomeric enzyme of ~100 kD. The polymerase binds specifically to a short (23 bp) promoter sequence with a specificity that prevents interference with expression of host genes. The coding region for the plastid-directed T7 RNA polymerase is operably linked to a tapetum-specific promoter, such that the gene will be transcribed only in taperum cells to induce cell death. The T7 polymerase-T7/lac promoter system is particularly advantageous for use in the present invention, inasmuch as high expression of the polymerase is not expected to cause any adverse effects on plant cells (expression of the T7 polymerase at levels as high as 1% of total cellular protein have been found not to adversely affect yeast growth (Chen et al., Cell, 50: 1047–1055, 1987)).

Thus, in this embodiment, the $A^N$ parental line expresses T7 RNA polymerase, the $A^P$ parental line contains the inactive pms gene in plastids, and the progeny of $A^N \times A^P$ are cytoplasmically male-sterile due to the interaction of the T7 polymerase on the T7/lac promoter, thereby activating the pms gene. These male-sterile progeny, the $A^S$ line, are used for production of hybrid seeds, as described above. For production of male-fertile hybrids, $A^S$ parents are crossed with $B^R$ parents, which express the rmf gene product, a plastid-targeted lac repressor. The lac repressor enters the plastid compartment and binds to the lac operator sequence included in the T7/lac promoter, thereby preventing transcription of the pms gene by the T7 RNA polymerase (see Dubendorff & Studier, J. Mol. Biol., 219: 45–49, 1991). Thus, hybrid $A^S B^R$ progeny will be male-fertile, that fertility being restored by expression of the rmf gene.

The T7/lac system described hereinabove is set forth in greater detail in Examples 1–3 and is schematically diagrammed in FIG. 1. In view of the above description of the T7/lac system, it will be appreciated that other activator and repressor systems may be utilized to obtain the same effects. For example, an alternative to the T7 RNA polymerase/lac repressor system is the T3 polymerase/lac repressor system described by Deuschle et al., Proc. Natl. Acad. Sci. USA, 86: 5400–5404 (1989).

Another system useful for practice of the invention is the tetracycline repressor and operator system, described below, which has been adapted for both mammalian and plant systems. (see Gossen et al., Trends in Biotechnology, 12: 58–62, 1994).

A. Plastid Male Sterility Genes for the "Pollen-Kill" Method

According to the "pollen-kill" method of the invention, the pms gene is introduced into the plastid as an inactive gene under control of a target sequence that enables expression of the gene only in the presence of the activator polypeptide encoded by the nms gene of the other parental component of the CMS line. In this embodiment, the pms gene coding region encodes a gene product (either RNA or protein) that is toxic to plastids in which it is produced. Because plastids are the sites of many important metabolic and biochemical processes of the plant, including photosynthesis (in chloroplasts), starch synthesis and accumulation (in chloroplasts and amyloplasts) and the synthesis of amino acids and lipids (in plastids generally), there are many targets in plastids for action of a plastid-toxic gene product. Examples of possible plastid-toxic systems include, but are not limited to: over-expression of specific plastid gene products, expression of antisense RNA or ribozymes directed to mRNAs encoding essential plastid gene products, post-transcriptional modification of vital proteins, e.g., ADP ribosylation (Ueda & Hayaishi, Ann. Rev. Biochem., 54: 73–100, 1985) heterologous DNAses, RNAses, proteases, and pore-forming proteins that make plastid membranes permeable, or otherwise disrupt the plastid membrane system. It should be noted that the toxic gene product may also leak (or be translocated) to the cytoplasm, where it may exert a toxic effect. Specific examples of useful lethal polypeptides include, but are not limited to:

T-urf13 from the CMS-T maize mitochondrial genome. As discussed in the Background Section, the 13 kDa polypeptide encoded by the urf13 gene increases the permeability of biological membranes, which leads to the CMS phenotype in naturally-occurring systems. See Hanson, Ann. Rev. Genet., 25:461–86 (1991). Other useful membrane disrupting proteins include various membrane transport proteins from yeast, bacteria or mammals (see, e.g., Ortiz et al., EMBO J., 11: 3491–3499, 1992; Guranka et al., FASEB J., 3: 2583–2592, 1989).

CytA toxin gene from *Bacillus thuringiensis* Israeliensis which encodes a hemolytic protein that kill mosquitos. Expression of the gene in plant cells causes death of the cell due to disruption of cellular membranes (McLean et al., J. Bacteriol., 169: 1017–1023, 1987; Ellar et al., U.S. Pat. No. 4,918,006, 1990), a biological activity that would also apply to organellar membranes, such as those of plastids.

Cre recombinase from bacteriophages P1 and the Cre-lox system, for generating site-specific recombination and rearrangements which can lead to loss of cellular viability (van Haaren & Ow, Plant Mol. Biol., 23: 525–533, 1993).

In this embodiment of the present invention, the coding region of the pms gene can also encode RNA capable of inhibiting a critical plastid function, thereby causing plastid disablement or death. These may include antisense molecules or ribozymes, the construction and use of which is known in the art. Antisense molecules are generally designed to bind to a critical region of a gene or mRNA, thereby preventing transcription or translation or triggering degradation of the target RNA. Ribozymes comprise a hybridizing region complementary in nucleotide sequence to a portion of the target RNA and a catalytic region that cleaves the target RNA at a specified location.

In the "pollen-kill" method, the regulatable target sequence of the pms gene contains a non-plastid promoter that is specifically activated by the plastid-directed gene product of the nms gene. In a preferred embodiment, the regulatable target sequence of the pms gene also comprises a repressor binding site located relative to the promoter, such that binding of a specific repressor to the repressor binding site prevents transcription of the gene, even in the presence of the activator polypeptide (referred to as a "controlling position" relative to the promoter and the pms coding region). Preferred for practice of the present invention is the T7/lac promoter construct described by Dubendorff and Studier, J. Mol. Biol., 219:45–49 (1991), and set forth above. Use of this promoter/repressor sequence enables activation of the pms gene by plastid-directed T7 RNA polymerase, and de-activation of the gene by a plastid-directed lac repressor for restoration of male fertility.

Another regulatable target sequence useful for practicing this embodiment is the tet repressor binding site (tet operator), also discussed above and hereinbelow in relation to the "pollen-starve" method. The lac operator or other repressor binding sites are similarly useful for systems employing chimeric activator polypeptides made up of a repressor binding domain and a heterologous activator domain.

B. Nuclear Male Sterility Genes for the "Pollen-Kill" Method

The nuclear male sterility genes of the present invention comprise three elements: (1) a coding region encoding the regulator polypeptide, translationally fused to (2) a plastid transit peptide enabling the regulator polypeptide to be translocated into plastids, transcription of the chimeric gene being under the control of (3) an anther-specific promoter.

Anther specificity is conferred to the CMS system of the invention by placing the coding region of the nms gene under control of an anther-specific promoter. An anther-specific promoter is one that directs the transcription of the associated coding sequence such that the corresponding messenger RNA is present in anther tissue in concentrations at least about 100-fold that observed in other tissues.

The metabolically active tapetum layer of the anther plays a nutritive role for microspores, the progenitors of pollen. Ablation of tapetal cells has been shown to result in nuclear male sterility. Mariani et al., Nature, 347: 737–741 (1990); Mariani et al., Nature, 357:384–387 (1992). Therefore, in a preferred embodiment of the present invention, tapetum-specific promoters are utilized. Taperum-specific promoters are known in the art, as exemplified by Mariani et al., 1990, 1992, supra. In another embodiment, microspore-specific promoters are utilized. Such promoters are also known in the art (e.g., T52 and T59, disclosed by Twell et al., Genes & Devel., 5: 496–507, 1991).

The nms gene may also comprise other regulatory signals. For example, a plant nuclear translational consensus sequence may also be included in the construct, as well as appropriate signals for termination of transcription and translation of plant nuclear genes.

Most plastid proteins are encoded in the nucleus, translated in the cytoplasm and post-translationally transported into the plastid. Such nuclear-encoded proteins are synthesized as higher molecular weight precursors that contain an N-terminal clearable sequence, referred to as a transit peptide. The transit peptide is necessary and sufficient for transport of the precursor polypeptide across the plastid envelope membrane (and, depending on the final location of the polypeptide into the various compartments of the plastid). Transit peptides are capable of directing the uptake and internal localization of heterologous passenger proteins translationally fused thereto. See generally, Theg & Scott, Trends in Cell Biology, 3: 186–190 (1993); See also Schnell & Blobel, J. Cell Biol., 120: 103–115 (1993); Kanefsky et al., Proc. Natl. Acad. Sci. USA, 91:1969–1973 (1994).

For practice of the present invention, a transit peptide directing translocation of the nuclear-encoded regulator polypeptide to the plastid stroma is utilized, since plastid genomes containing the pms gene are stromally located. In a preferred embodiment, a DNA sequence encoding the transit peptide of the ribulose-1,5-bisphosphate carboxylase/oxygenase (RuBisCO) small subunit precursor (pre-SS) is incorporated into the nms gene for the purpose of expressing a precursor polypeptide comprising the regulator polypeptide translationally fused to the pre-SS transit peptide. Although the pre-SS transit peptide is exemplified herein, it will be appreciated by those skilled in the art that any transit peptide directing a stromally-localized nuclear-encoded protein will be useful for practice of the present invention.

In the "pollen-kill" method, the nms gene encodes a plastid-directed activator polypeptide capable of activating a toxic pms gene by way of the target nucleotide sequence operably linked to the gene. Activator polypeptides of the invention include, but are not limited to, polymerases, DNA binding proteins, naturally occurring and synthetic transcriptional activators, translational activators, other post-transcriptional activators, and the like. The use of an activator polypeptide to direct expression of another nucleotide sequence is exemplified by the T7 RNA polymerase, as described above. See U.S. Pat. No. 5,122,457 to Reim et al. and U.S. Pat. No. 4,952,496 to Studier et al., as well as the review of Studier et al., Meth. Enz., 185: 60–89 (1990).

The activator polypeptide of the invention may also comprise other DNA binding proteins necessary for transcription activation of specific promoters (e.g., phage T3 RNA polymerase). Additionally, the binding domain of one protein may be fused to a transcription activation domain of another protein. An example of such a chimeric protein is a tetR/VP16 transcriptional activator described in a review by Gossen et al., Trends in Biotech, 12: 58–62 (1994). Other examples of chimeric transcriptional activators include the Lex A (binding domain)/Gal4 transcriptional activator described by Brent & Ptashne, Cell, 43: 729–736 (1985) and Gal4/VP16 (Carey et al., J. Mol. Biol., 209: 423–432, 1989; Cress et al., Science, 251: 87–90, 1991; Sadowski et al., Nature, 335: 563–564, 1988).

Translational activators may also be utilized in the present invention. Leader sequences and specific translational activators thereof directing high expression of viral genes are particularly useful. One example is the cauliflower mosiac virus translational activator (TAV), as described by Futterer & Hohn, EMBO J., 10: 3887–3896 (1991). In such a system, the pms gene may be constructed to encode a dicistronic message wherein, e.g., the first cistron may be the selectable marker gene and the second cistron may be the plastid lethal gene, both transcribed in the same mRNA from the same promoter. Translation of the selectable marker mRNA occurs without the addition of other components; however, the plastid-lethal mRNA will not be translated unless TAV is present.

C. Restorer of Male Fertility Genes for the "Pollen-Kill" Method

The rmf gene product may prevent action of the nms gene at any one of several points, including, but not limited to: (1) in plastids at the pms gene, e.g., by interfering with transcription or translation of a plastid-toxic pms gene or by de-repression of an essential pms gene that has been inactivated by an nms-encoded repressor; (2) in plastids, but not necessarily at the pms gene, by interfering with or destroying the mature regulator polypeptide; (3) in the cytoplasm by interfering with or destroying the precursor regulator polypeptide before it has been translocated into chloroplasts; and (4) in the cytoplasm or nucleus by interfering with expression of the nms gene (e.g., by way of a transcriptional or translational repressor).

The rmf genes of the present invention comprise at least a coding region encoding the restorer gene product, operatively linked to appropriate 5' and 3' regulatory sequences for expression from the nuclear genome. The regulatory sequences necessary to include in the rmf gene depend upon the point in regulator polypeptide action at which the rmf gene product is designed to interfere, as described above.

Anther-specificity of the rmf gene product is not absolutely necessary for practice of the present invention; the rmf gene could be expressed in other tissues, as long as it is also expressed in the anther tissues expressing the nms gene. However, anther specificity is preferred for practice of the present invention inasmuch as systematic expression of the rmf gene throughout the plant may produce a toxic effect, which is often observed in relation to expression of a foreign gene in host cells. Moreover, the inclusion of a strong anther-specific promoter in the rmf gene, preferably the same or a similar promoter as that used for the nms gene, will ensure strong expression of the rmf gene and production of the rmf gene product at the location where the nms gene is also being expressed. Accordingly, the rmf gene of the invention comprises the restorer polypeptide coding region operably linked to an anther-specific promoter, such as those described above for the nms gene.

The rmf gene may also comprise other regulatory signals. For example, a plant nuclear translational consensus sequence may also be included in the construct, as well as appropriate signals for termination of transcription and translation of plant nuclear genes.

If the rmf gene product is a restorer polypeptide destined for the plastid stromal compartment, the coding region of the rmf gene must be linked to a DNA sequence encoding a plastid stromal transit peptide, such as the pre-SS transit peptide described relative to the nms gene above. DNA sequences encoding other transit peptides for translocation of proteins to the plastid stroma are also known in the art and may be utilized in practice of this aspect of the invention.

In a preferred embodiment of the "pollen-kill" method, the rmf gene encodes a plastid-directed polypeptide that enters plastids and interferes with action of the nms encoded regulator polypeptide by exerting an overriding opposing regulation of the pms gene. This embodiment is exemplified by an rmf gene that encodes a plastid-directed lac repressor polypeptide. The pms gene comprises a lac repressor binding site located relative to the activatable target nucleotide sequence and the pms coding region such that binding of the lac repressor inhibits transcription of the pms gene, in spite of the presence of the nms-encoded activator polypeptide (e.g., T7 RNA polymerase).

As described above, numerous transcriptional and translational repressor systems are known in the art. These other repressor proteins may also be utilized as the rmf-encoded restorer polypeptide. Additionally, chimeric proteins comprising DNA binding domains from one polypeptide with repressor domains from another polypeptide may also be utilized, as described above for activator polypeptides.

In other embodiments utilizing a plastid-directed restorer polypeptide, the restorer polypeptide may be a protein capable of specifically binding to the regulator polypeptide, thereby preventing its action on the pms gene, such as plastid-directed immunoglobulins or fragments therof, or other specific ligands associated with repressor activator systems known in the art (e.g., an enzyme that generates a small molecule inducer that binds to the repressor and renders it inactive).

In an alternative embodiment, applicable to either the "pollen-kill" or the "pollen-starve" method, the rmf gene encodes a cytoplasmic polypeptide that prevents the nms-encoded regulator polypeptide precursor from entering plastids. Proteins that can be used for this embodiment include, but are not limited to, immunoglobulins or fragments thereof that are specific for the precursor regulator polypeptide and proteases or other protein-modifying enzyme capable of specifically acting on the precursor regulator polypeptide and rendering it incapable of crossing the plastid membranes, or translational terminators that prevent translation of the nms-encoded mRNA.

In another embodiment, the rmf gene encodes a nucleus-targeted polypeptide, such as a transcriptional or translational repressor, capable of entering the nucleus and preventing expression of the nms gene. To practice this embodiment of the invention, the nms gene should comprise a repressor binding site for the rmf-encoded repressor. Relative to this embodiment, it should be noted that eucaryotic nuclei, including plant nuclei, contain a set of proteins which are synthesized in the cytoplasm and translocated to the nucleus through the operation of amino acid signal sequences contained within those proteins. Such localization signals for targeting proteins to the nucleus are well known in the art. See, e.g., Hall et al., Cell, 36: 1057–1065 (1984) (describing targeting of bacterial β-galactosidase to the yeast nucleus via a nuclear localization sequence from the yeast MAT alpha 2 gene).

II. THE "POLLEN-STARVE" METHOD

In another embodiment, referred to herein as the "pollen-starve" method, the pms gene is a homolog of a native plastid gene essential for plastid survival, which is active but which has been modified to be inactivatable (i.e., repressible). The native plastid gene is replaced by the modified pms gene by homologous recombination, such that stably plastid-transformed plants contain only the modified form of the gene. The nms gene in this embodiment is an anther-specific gene that encodes a plastid-directed inactivator polypeptide capable of entering plastids and blocking expression of the essential pms gene, thereby disabling or killing the plastids of the selected anther tissue. The rmf gene of the B parent again encodes a "restorer" gene product capable of interfering with the action of the inactivator polypeptide, thereby enabling the essential pms gene to remain active. In a preferred embodiment, the rmf gene encodes a nuclear directed polypeptide capable of entering the nucleus and interfering with expression of the nms gene. In another embodiment, the rmf gene encodes a cytoplasmic gene product that interferes with translation of mRNA encoding the inactivator polypeptide or translocation of the precursor into plastids.

The "pollen-starve" method is exemplified by a system utilizing a plastid-targeted lac repressor as the inactivator polypeptide, a nuclear-targeted tet repressor as the rmf gene product and an essential plastid gene operably linked to requisite 5' and 3' regulatory sequences necessary for its expression in plastids, under the control of at least one lac repressor binding site.

In this embodiment, the $A^N$ parental line expresses a plastid-targeted lac repressor polypeptide, the $A^P$ parental line contains the active modified pms gene in plastids, and the progeny of $A^N \times A^P$ are cytoplasmically male-sterile due to the binding of the lac repressor to the lac repressor binding site, thereby preventing expression of the essential pms gene. For production of male-fertile hybrids in this embodiment, $A^S$ parents are crossed with $B^R$ parents, expressing the rmf gene product, a nuclear-targeted tet repressor.

The tet repressor system should prove particularly useful in plants, as it has already been shown in transgenic tobacco that the tetracycline repressor can repress transcription from a cauliflower mosaic virus promoter containing three tet repressor binding sites in close proximity to the promotor TATA-box. The repression was rapidly reversed by tetracycline, resulting in a regulation factor of several-hundred fold (Gatz et al., Plant J., 2: 397–404, 1992; Gatz & Quail, Proc. Natl. Acad. Sci. USA, 85: 1394–1397, 1988).

The tetracycline repressor described above may also be used as the nms gene product in the practice of the "pollen-starve" method of the invention. In this embodiment, the inactivator polypeptide comprises a plastid-targeted tet repressor. The pms gene comprises at least one tet repressor binding site located relative to the intrinsic plastid 5' and 3' regulatory regions such that binding of the tet repressor blocks expression of the pms gene. As described above, male-fertility is restored in hybrids by transforming the B parental line with an rmf gene encoding another nuclear-targeted repressor, such as the lac repressor or a different tet repressor. It should be noted that the plastid-targeted repressor and the nuclear-targeted repressor may be selected from two different repressor families, as described hereinabove (the lac repressor targeted to plastids and the tet repressor targeted to nuclei, or vice-versa). This method may also be practiced using the same repressor, translationally fused to either a plastid-targeting sequence or a nuclear-targeting sequence. However, the use of two different repressors is preferred for practice of the invention.

A. Plastid Male Sterility Genes for the "Pollen-Starve" Method

In the "pollen-starve" method of the invention, an essential plastid gene is replaced by a homologous gene which has been modified to be inactivatable. The modified gene is stably integrated into the plastid genome by homologous recombination, as described above. Essential plastid genes useful for practice of this embodiment of the invention include: the ribosomal RNA operon, the rps16 ribosomal protein gene, the trnV gene and the rpoB gene. Because the pms gene in this case is introduced into the plastid in an active form, the pms gene must also comprise natural plastid promoters and other regulatory sequences necessary for expression of the pms gene in plastids.

In a preferred embodiment, the pms gene comprises the lac repressor binding site described above. The repressor binding site is located relative to the natural plastid promoter sequences controlling transcription of the pms gene such that binding of a lac repressor inhibits transcription of the essential gene, thereby resulting in plastid disablement or death. Fertility may be restored by a mechanism for interfering with synthesis of the plastid-targeted deactivator polypeptide in the nucleus or cytoplasm. Other repressor binding sites useful for this embodiment of the invention include, but are not limited to, the tet repressor binding site, the LexA binding site (Brent & Ptashue, Cell, 43: 729–736, 1985), and the Gal4 binding site.

B. Nuclear Male Sterility Genes for the "Pollen-Starve" Method

In the "pollen-starve" method, the nms gene encodes a plastid-targeted "inactivator" polypeptide which prevents expression of the essential pms gene in the plastid. The inactivator polypeptide may comprise a transcriptional or translational repressor, numerous examples of which are known in the art. In a preferred embodiment, a lac repressor protein is encoded by the nms gene. The protein enters chloroplasts and binds to the lac repressor binding site, linked to the pms gene in such a way that binding of the repressor protein to the binding site inhibits transcription of the pms gene, thereby causing plastid death.

Other transcriptional repressor proteins useful for practice of the present invention include, but are not limited to, the tet repressor described hereinabove. Chimeric proteins comprising DNA binding domain from one polypeptide with repressor domains from another polypeptide may also be utilized as described above for activator polypeptides.

C. Restorer of Male Fertility Genes for the "Pollen-Starve" Method

As described above, the rmf gene product may prevent action of the nms gene at any one of several points between expression of the nms gene and action of the nms encoded polypeptide on the pms gene. The restorer of male fertility genes of the present invention comprise at least a coding region encoding the restorer gene product, operatively linked to appropriate 5' and 3' regulatory sequences for expression from the nuclear genome. The regulatory sequences necessary to include in the rmf gene depend upon the point in regulator polypeptide action at which the rmf gene product is designed to interfere, as described above.

As mentioned earlier, anther-specificity of the rmf gene product is not absolutely necessary, but is preferred for practice of the present invention. Accordingly, the rmf gene comprises the restorer polypeptide coding region operably linked to an anther-specific promoter, such as those described above for the nms gene.

The rmf gene may also comprise other regulatory signals. For example, a plant nuclear translational consensus sequence may also be included in the construct, as well as appropriate signals for termination of transcription and translation of plant nuclear genes.

In an embodiment particularly preferred for the "pollen-starve" method, the rmf gene encodes a nucleus-targeted polypeptide, such as a transcriptional repressor, capable of entering the nucleus and preventing expression of the nms gene. To practice this embodiment of the invention, the nms gene should comprise a repressor binding site for the rmf-encoded repressor. Relative to this embodiment, it should be noted that eucaryotic nuclei, including plant nuclei, contain a set of proteins which are synthesized in the cytoplasm and translocated to the nucleus through the operation of amino acid signal sequences contained within those proteins. Such localization signals for targeting proteins to the nucleus are well known in the art. See, e.g., Hall et al., Cell, 36: 1057–1065 (1984) (describing targeting of bacterial β-galactosidase to the yeast nucleus via a nuclear localization sequence from the yeast MAT alpha 2 gene).

In an alternative embodiment, the rmf gene encodes a cytoplasmic polypeptide that prevents the nms-encoded regulator polypeptide precursor from entering plastids. Proteins that can be used for this embodiment include, but are not limited to, immunoglobulins or fragments thereof that are specific for the precursor regulator polypeptide and proteases or other protein-modifying enzyme capable of specifically acting on the precursor regulator polypeptide and rendering it incapable of crossing the plastid membranes, or translational terminators that prevent translation of the nms-encoded mRNA.

In the embodiment of interfering with expression of the rims gene, it will also be appreciated by those of skill in the art that the rmf gene may encode an RNA molecule capable of preventing transcription or translation of the nms gene or mRNA. Such an mRNA molecule may be an antisense oligonucleotide that specifically binds to a critical region of the nms gene or mRNA. Alternatively, the RNA molecule may be a ribozyme capable of binding to a selected location on the nms-encoded mRNA, thereby cleaving the mRNA molecule and preventing translation thereof.

The transgenic CMS seed production system of the present invention is similar in structure to naturally occurring and conventional CMS-based schemes. However, the systems of the invention represent a marked improvement over those systems, inasmuch as they are assembled from elements fully characterized at the DNA sequence level and utilize plastids as the basis for cytoplasmic male sterility instead of mitochondria. In contrast to mitochondria and the mitochondrial genome, the plastid genome is well characterized, and methods for genetic manipulation of plastids are much better developed than those relating to mitochondria. As a result, the plastid-based CMS system of the invention is substantially free from the unpredictable deleterious characteristics associated with mitochondrial-based CMS systems, and is applicable to any crop amenable to nuclear and plastid transformation technology. As such technology continues to expand to include new crop species, the novel CMS methods of the invention may be applied to those crops. Thus, the systems of the present invention will make hybrid seed production more cost effective and will enable development of hybrids in crops for which no practical hybrid seed production is currently available. Such crops include major agronomic crops of the United States, including wheat and cotton.

The following examples are provided to describe the invention in further detail. These examples are intended to illustrate and not to limit the invention.

EXAMPLE 1

Pollen-Kill Method of Plastid Male Sterility: The Kpms Plastid Male Sterility Genes The "pollen-kill" method of the invention is shown schematically in FIG. 1. In a preferred embodiment of the "pollen-kill" method, the plastid "killer" gene (Kpms) is expressed from a regulated T7/lac promoter which contains the T7 phage gene 10 promoter and the lacI operator so that transcription can be blocked by the lac repressor (Studier et al., 1990, supra; Dubendorf & Studier, 1991; supra). The promoter sequences shown in FIG. 3 are modified from the pET21d expression plasmid (Novagen). Referring to FIG. 3, PT71acl has the untranslated gene 10 leader sequence, including the ribosome binding site (RBS). PT71ac2 has the leader sequence and the RBS of the plastid rbcL gene. The two promoters are transcribed at comparable efficiencies. However, the mRNAs with the gene 10 leader are translated ~2,000 times more efficiently than those containing the rbcL leader. A relatively low level of translation is preferable in the "pollen-kill" method, to prevent lethal accumulation of the toxic gene product from any low level transcription originating from outside promoters. Such rare transcripts, if effectively translated, would have an adverse effect on non-target tissues.

To stabilize the mRNA, the Kpms gene coding region is ligated to a modified T7 gene 10 terminator (TT7), or to terminator Trps16T7, which comprises the plastid rps16 ribosomal protein gene 3' trailer sequence and the T7 gene 10 terminator in a tandem arrangement (FIG. 3).

Toxic genes that are suitable for disrupting plastid function are listed in the Detailed Description above. For convenient expression in the cassettes, the Kpms genes should have: (i) an NcoI restriction site, including the translational initiation codon (ATG) and (ii) an XbaI site immediately downstream of the coding region. However, alternative cloning strategies may also be applied that are well known in the art.

Figure 4:
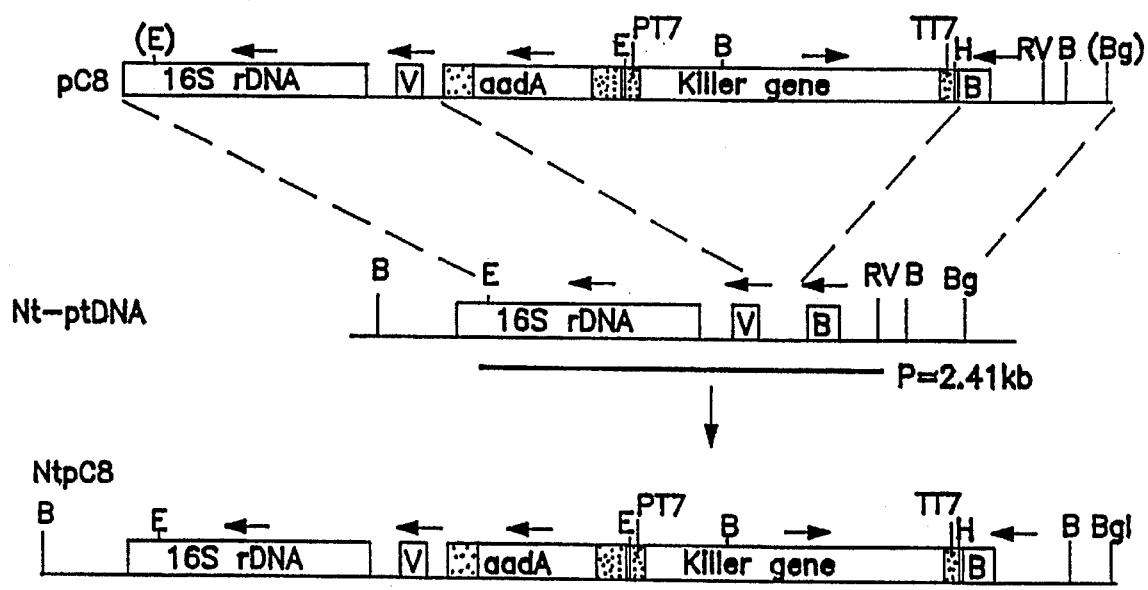
FIG. 4. Integration of the Kpms gene into a transcriptionally silent region of the plastid genome by linkage to the spectinomycin resistance (aadA) gene. The plastid targeting region of plasmid pC8 is shown, as is the cognate region in the wild-type plastid genome (Nt-ptDNA), and the region containing the integrated killer gene. Integration of aadA and the passenger gene is by two homologous recombination events between the dashed lines. Abbreviations: 16SrDNA= 16SrRNA gene; V=trnV gene; B=ORF70B open reading frame; PT7 =PT71acI promoter; TT7 =TT7 terminator. Restriction sites: E, EcoRI; B, BamHi; Bg, BglII; H, HindIII; RV, EcoRV.

To minimize the possibility of incoming transcripts from outside promoters, integration of the Kpms genes should be into a transcriptionally silent region of the plastid genome. The most suitable position is between the trnV and ORF70B genes, directing the transcription of the killer gene towards the rps12/7 operons, as shown diagramatically in FIG. 4 for the insertion vector labelled "pC8". Transformation and selection of plastid transformants is carried out by standard protocols (Svab and Maliga, 1993, supra).

EXAMPLE 2

Pollen-Kill Method of Plastid Male Sterility: The Knms Nuclear Male Sterility Genes The "pollen-kill" method of plastid male sterility depends on transcription of the Kpms plastid gene in tapetal cells. The success of the strategy depends upon: (i) the developmental timing and tissue specificity of expression of the Knms gene encoding the T7 RNA polymerase and (ii) the targeting of the encoded polypeptide to plastids.

Developmental timing of the Knms gene is achieved by the utilization of taperum-specific or microspore-specific promoters. Suitable for the purpose is the TA29 promoter, which is transcribed transiently during early anther development. The TA29 promoter has been utilized to obtain taperum-specific gene expression and subsequent male sterility by expressing a chimeric ribonuclease (Mariani et al., 1990, supra). Additional suitable characterized anther-specific promoters for the expression of the nuclear nms gene are available from several sources (see the review of Goldberg et al., Plant Cell, [: 1217–1229, 1993).

Figure 5:
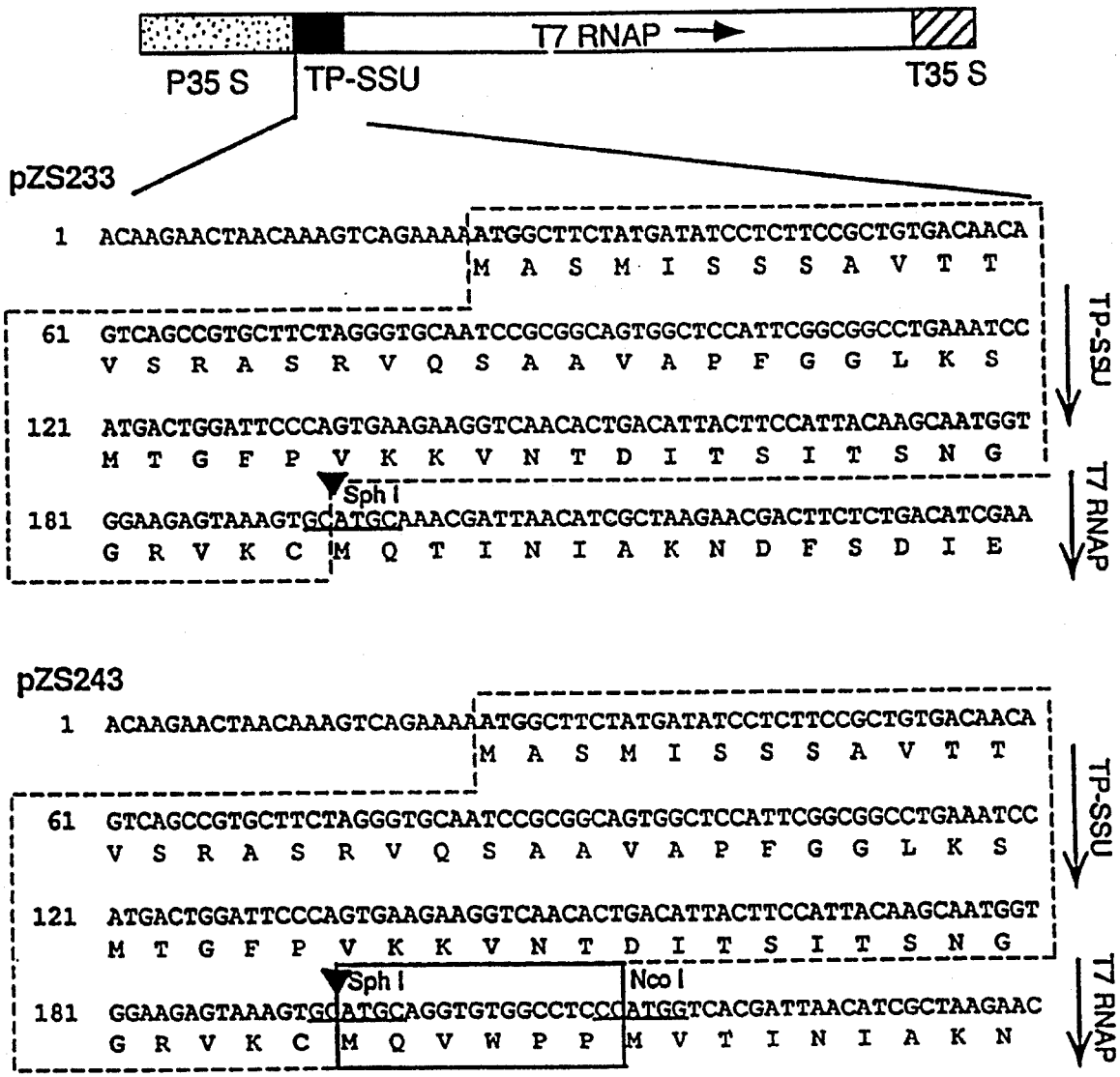
FIG. 5. Knms nuclear male sterility genes (pZS233: nucleotide sequence is Sequence I.D. No. 5, protein sequence is Sequence I.D. No. 6; pZS243: nucleotide sequence is Sequence I.D. No. 7, protein sequence is Sequence I.D. No. 8). The Knms genes shown are expressed as constitutive genes, with a cauliflower mosaic virus 35S promoter (P35S; Timmermans et al., J. Biotechnol., 14: 333-344, 1990), RuBisCO small subunit transit peptide (TP-SSU; Kanevski & Maliga, Proc. Natl. Acad. Sci. USA, 91: 1969–1973, 1994), T7 RNA polymerase (T7-RNAP; Studier et al., Meth. Enz., 185: 60–89, 1990) and cauliflower mosaic virus transcriptional terminator (T35S; Timmermans et al., 1990, supra). Protein sequence of the transit peptide (in dashed lines) and the N-terminal fusion with T7 RNA polymerase are also shown. The processing site is marked by a filled triangle. Processing of preT7RNAP yields T7RNAP without additional amino acids when expressed from the pZS233 gene shown above, and leaves 5 amino acids of the mature SSU fused at the N-terminus when expressed from the pZS243 gene shown below.

Referring to FIG. 5, The T7 RNA polymerase coding region in the Knms gene is translationally fused with the transit peptide of a nuclear-encoded chloroplast protein, the small subunit of RuBisCo (SSU). When the Knms gene is expressed in the nucleus, the transit peptide targets the protein to plastids. Upon import into plastids the transit peptide is cleaved from the T7 pre-protein (preT7RNAP) to yield the T7 RNA polymerase (T7RNAP) without any additional amino acids. The DNA sequence encoding the SSU transit peptide and the junction of the T7 protein fusion are shown in FIG. 5 (Upper). The preT7aRNAP in a second gene (FIG. 5, Lower sequence) is processed to T7aRNAP in plastids. The T7aRNAP contains five amino acids of the mature SSU. Proteins encoded in the two genes may differ with respect to their efficiency of import, and may be used to obtain transgenic plants accumulating the T7 RNA polymerase at different levels.

Plants expressing the T7 RNA polymerase do not have a distinct phenotype. To facilitate the identification of plants carrying Knms, the gene is linked to a selectable kanamycin resistance gene in an Agrobacterium binary vector (for example the pBI121 vector plasmid; Clonetech). Alternatively, plasmids that carry the Knms genes are mixed with plasmids that carry a selectable kanamycin resistance gene: for example, plasmid pLGVneol103 (Czernylowski et al., DNA, 5: 101–103, 1986) or plasmid pFF19K (Timmermans et al., 1990, supra). Biolistic transformation with mixed DNA, followed by selection for kanamycin resistance, is used to achieve simultaneous integration of both genes at the same genetic locus. Co-segregation of kanamycin resistance and the T7 polymerase genes verifies that the two genes are integrated at the same genetic locus.

EXAMPLE 3

Pollen-Kill Method of Plastid Male Sterility: The Krmf Nuclear Restorers of Male Fertility Plastid male sterility is the phenotype of plants that carry both the plastid Kpms and nuclear Knms genes. Restoration of male fertility depends on the presence of a second nuclear gene, Krmf, the restorer of fertility preferably used for the "pollen-kill" type plastid male sterility. Krmf exerts its effect by blocking the expression of the plastid Kpms gene (FIG. 1). This regulation is mediated via the Kpms gene promoter region.

The PT71acl and pT71ac2 promoters shown in FIG. 3 can be regulated: (i) positively, by the plastid-targeted T7 RNA polymerase (above) and (ii) negatively, by the lac repressor. Restoration of male fertility depends on the presence of lac repressor in plastids in sufficient concentration to block activity of the Knms gene product.

Expression of the Krmf gene prior to, and during the expression of the nuclear male sterility gene, Knms, is important for the full restoration of male sterility. The most simple and effective way to achieve this is by expressing the encoded lac repressor protein from a constitutive promoter, such as the anther box-containing cauliflower mosaic virus 35S promoter in construct pTS24 (van der Meer et al., Plant Cell, 4: 253–262, 1992). Alternatively, transcription may be directed by the promoter of an anther-specific gene which is activated prior to the expression of the Knms gene. Characterized anther-specific promoters suitable for driving the expression of the nuclear restorer gene are available from several sources as reviewed by Goldberg et al., 1993, supra. In addition, restoration of nuclear male sterility was also feasible using the same (TA29) promoters to express both the sterility-inducing and fertility-restoring transgenes (Mariani et al., 1992).

Figure 6:
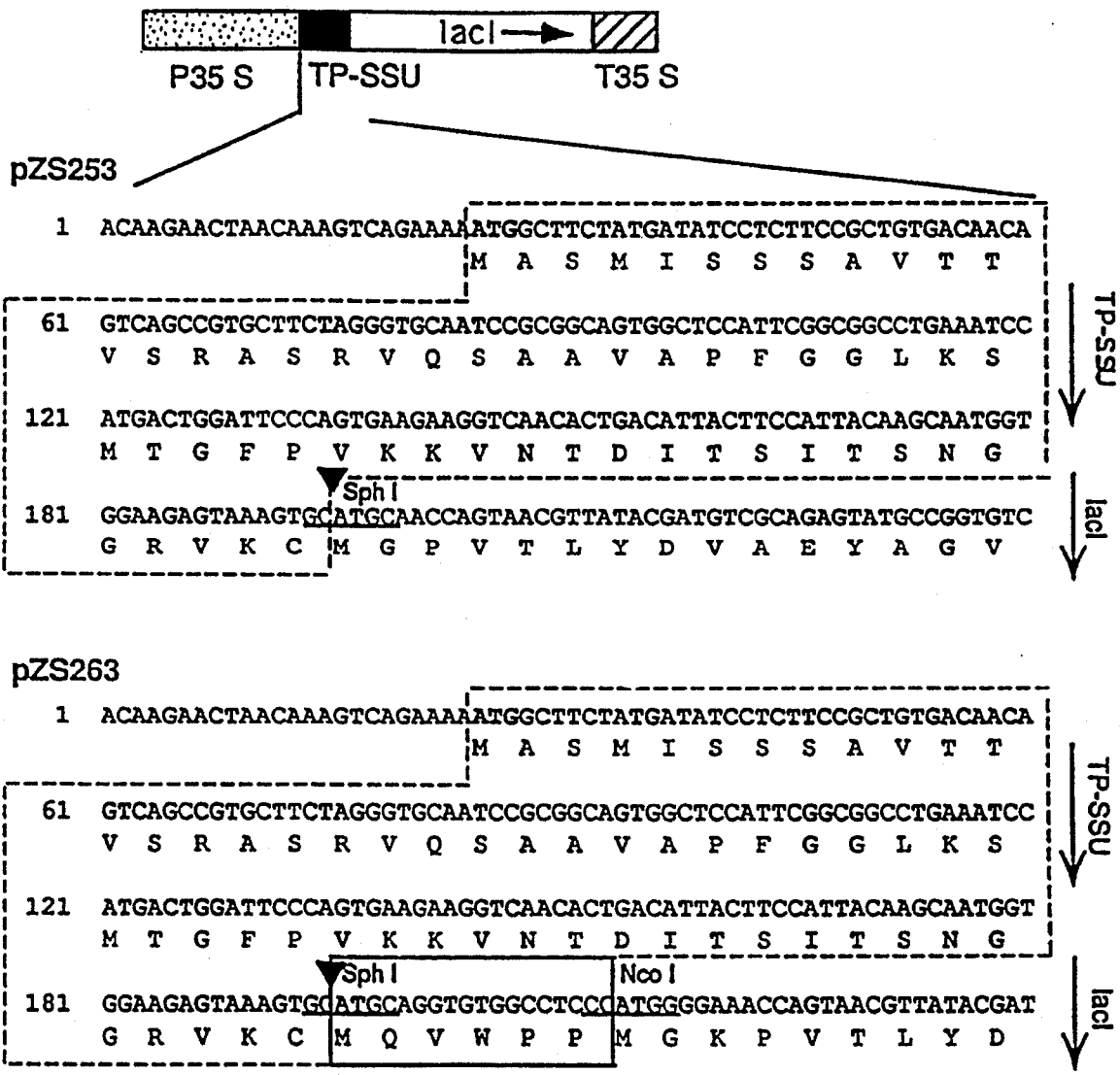
FIG. 6. Srm# nuclear restorer of male fertility genes (pZS253: nucleotide sequence is Sequence I.D. No. 9, protein sequence is Sequence I.D. No. 10; pZS263: nucleotide sequence is Sequence I.D. No. 11, protein sequence is Sequence I.D. No. 12). A constitutive test gene, with a cauliflower mosaic virus 35S promoter (P35S; Timmermans et al., 1960, supra) is shown. TP-SSU, RuBisCO small subunit transit peptide (Kanevski & Maliga, 1994, supra); lacI, lac repressor coding region (Farabaugh, Nature, 274: 765–769, 1978); T35S, the cauliflower mosaic virus transcriptional terminator (Timmermans et al., 1990, supra). Protein sequence of the transit peptide (in dashed lines) and the N-terminal fusion with T7 RNA polymerase are also shown. The processing site is marked by a filled triangle. Processing of preT7RNAP yields T7RNAP without additional amino acids when expressed from the pZS253 gene depicted above, and leaves 5 amino acids of the mature SSU fused at the N-terminus when expressed from the pZS263 gene shown below.

To target the lac repressor to plastids, it is fused to the RuBisCo small subunit transit peptide. The gene design, and the DNA and protein sequence of the critical transit peptide and lacI coding region fusion are shown in FIG. 6, and are as discussed for the Knms gene above. It should be noted that the diagram in FIG. 6 shows expression from a constitutive tissue non-specific promoter, P35S (Timmerman et al., 1990, supra). However, for anther-specific expression, an anther box-containing derivative should be utilized (e.g., PTS24, van den Meer et al., 1992, supra).

When introduced into the nuclear genome, the Krmf gene is linked to a selectable gentamycin resistance marker encoded in a chimeric aacCl gene (Carrer et al., Plant Mol. Biol., 17: 301–303, 1991). The methods of transformation are identical with those described for the Knms gene. The gentamycin resistance gene linked to the Krmf gene is readily distinguishable from the kanamycin resistance gene linked to Knms, and from the spectinomycin resistance gene linked to the plastid Kpms gene.

EXAMPLE 4

Pollen-Starve Method of Plastid Male Sterility Spms Plastid Male Sterility Genes Due to the requirement for intact organelles to maintain amino acid and lipid biosynthesis, elimination of protein synthesis in plastids leads to cellular death. Therefore, blocking the expression of genes required for plastid maintenance can also be used to ablate tapetal cells or microspores.

The plastid male sterility genes of the "pollen-starve" method (Spms) are endogenous plastid genes expressed from chimeric plastid promoters with an incorporated lac repressor binding site. These promoters in somatic cells are transcribed by the plastid RNA polymerase. However, expression of the plastid genes in the tapetum cell is prevented by the lac repressor, which is engineered to be expressed only in the tapetum, microspores or other anther cells. The rRNA operon is a preferred target for repression in the "pollen starve" method. Modified rRNA operon promoters and the trnV gene promoter with a lac operator sequence are shown in FIG. 7. These promoters are used to replace the cognate endogenous gene promoters by homologous recombination. Derivatives of the rRNA operon promoter modified for protein expression are shown in FIG. 8. The two promoters differ with respect to their leader sequence (ribosome binding site). Of the two promoters, mRNAs with the gene 10 leader sequence are likely to be translated more efficiently.

Endogenous gene promoters are replaced with the Spms promoters by linkage to a selectable spectinomycin resistance (aadA) gene (Maliga et al., 1993). The Spms genes are transcribed by the plastid RNA polymerase in all tissues except the tapetum cells, in which a plastid-targeted lac repressor is produced from the Snms gene. The plastid-targeted lac repressor blocks transcription from the Spms promoters, thereby causing cell death.

EXAMPLE 5

Pollen-Starve Method of Plastid Male Sterility: The Snms Nuclear Male Sterility Genes As described in Example 4, pollen male sterility in the "pollen-starve" method is achieved by blocking the transcription of an endogenous plastid gene. Lack of transcription is due to accumulation of the lac repressor in plastids, and its binding to the lac operator sequences in the chimaeric promoter of the Spms gene. Tissue-specific expression of the lac repressor is achieved using anther-specific promoters, as described for the Knms gene (Example 2). The Snms promoter, however is sensitive to the tetracycline (tet) repressor so that expression of the Snms gene can be prevented by a Srmf gene encoding a nuclear-targeting tet repressor (see Example 6). The Snms genes are genetically linked to kanamycin resistance markers as described for the Knms gene (Example 2).

EXAMPLE 6

Pollen-Starve Method of Plastid Male Sterility: The Srmf Nuclear Male Sterility Genes Restoration of male fertility requires restoration of the normal activity of the Spms gene in plastids of the tapetum cells. This can be best achieved by blocking the expression of the nuclear Snms gene. The Snms gene is expressed from an anther-specific promoter, which also contains copies of the 19 bp pallindromic tet operator. The fertility restorer gene of the system, Srmf, encodes the tet repressor which is targeted to the nucleus, and down-regulates the expression of the Snms gene 500 fold. This system has been described by Gatz et al., Plant J., 2: 397–404 (1992). The Srmf gene is linked to a gentamycin resistance gene so that it can be readily distinguished from plants carrying the Spms gene (linked to spectinomycin resistance) and Snms genes (linked to kanamycin resistance).

What is claimed is:

1. A method for producing cytoplasmically male-sterile plants, said method comprising:

a) providing a parent plant line;

b) producing a plastid-transgenic parent plant from said parent plant line by stably transforming plastids in cells of said parent plant line with a plastid male sterility gene and regenerating a plastid-transgenic plant therefrom, said plastid male sterility gene being capable of regulation by a nuclear-encoded plastid-directed regulator polypeptide, said regulation in anther tissue causing disruption of formation of viable pollen;

c) producing a nuclear-transgenic parent plant from said parent plant line by stably transforming nuclei in cells of said parent plant line with a nuclear male sterility gene and regenerating a nuclear-transgenic plant therefrom, said nuclear male sterility gene comprising an anther-specific 5' regulatory nucleotide sequence operably linked to a coding nucleotide sequence that encodes said plastid-directed regulator polypeptide, which is capable of entering plastids and regulating said plastid male sterility gene; and d) crossing said plastid-transgenic plant with said nuclear-transgenic plant to produce a plant in which said plastid-directed regulator polypeptide is anther-specifically produced, enters said transformed plastids of anther cells and regulates said plastid male sterility gene, said regulation causing disruption of formation of viable pollen, thereby producing said cytoplasmically male-sterile plants.

2. A method according to claim 1, wherein said anther-specific 5' regulatory nucleotide sequence is selected from the group consisting of taperum-specific promoters and microspore-specific promoters.

3. A method according to claim 1, wherein:

a) said plastid male sterility gene comprises a target nucleotide sequence for activating gene expression, operably linked to a coding nucleotide sequence that encodes a gene product capable of disrupting said formation of viable pollen when expressed in plastids of anther cells; and b) said nuclear male sterility gene encodes a plastid-directed activator polypeptide that enters plastids and specifically interacts with said target nucleotide sequence, said interaction causing expression of said plastid male sterility gene.

4. A method according to claim 3, wherein said plastid male sterility gene encodes RNA.

5. A method according to claim 4, wherein said RNA is selected from the group consisting of antisense RNA and ribozymes.

6. A method according to claim 3, wherein said plastid male sterility gene encodes a polypeptide.

7. A method according to claim 6, wherein said polypeptide is selected from the group consisting of DNAses, RNAses, proteases, recombinases and transmembrane pore-forming polypeptides.

8. A method according to claim 3, wherein said plastid-directed activator polypeptide comprises a transcriptional activator and said target nucleotide sequence comprises a regulatory region to which said transcriptional activator binds.

9. A method according to claim 8, wherein said transcriptional activator is a polymerase.

10. A method according to claim 9, wherein said polymerase is a T7 RNA polymerase and said target nucleotide sequence comprises a T7 promoter.

11. A method according to claim 8, wherein said transcriptional activator is a chimeric protein comprising a DNA binding domain and an activator domain.

12. A method according to claim 3, wherein said plastid-directed activator polypeptide comprises a translational activator and said target nucleotide sequence comprises a regulatory region to which said translational activator binds.

13. A method according to claim 1, wherein:
   a) said plastid male sterility gene comprises a target nucleotide sequence for preventing gene expression, operably linked to an essential plastid gene, expression of which is necessary for plastid survival or function, said plastid male sterility gene being targeted to a plastid genome such that native forms of said essential plastid gene in transformed plastids are replaced with said plastid male sterility gene, prevention of expression of said plastid male sterility gene in plastids of anther cells being capable of disrupting said formation of viable pollen; and
   b) said nuclear male sterility gene encodes a plastid-directed inactivator polypspride that enters plastids and specifically interacts with said target nucleotide sequence for preventing gene expression, said interaction preventing expression of said plastid male sterility gene.

14. A method according to claim 13, wherein said essential plastid gene is selected from the group consisting of a ribosomal RNA operon, a 16S ribosomal protein gene, a trnV gene and a rpoB gene.

15. A method according to claim 13, wherein said plastid-directed inactivator polypeptide comprises a transcriptional repressor and said target nucleotide sequence comprises a regulatory region to which said transcriptional repressor binds.

16. A method according to claim 15, wherein said transcriptional repressor is a lac repressor and said target nucleotide sequence comprises at least one lac repressor binding site.

17. A method according to claim 13, wherein said inactivator polypeptide is a chimeric protein comprising an DNA binding domain and a repressor domain.

18. A method according to claim 13, wherein said plastid-directed inactivator polypeptide comprises a translational repressor and said target nucleotide sequence comprises a regulatory region to which said translational repressor binds.

19. A method for producing male-fertile hybrid seed from two parent plant lines, one of which comprises cytoplasmically male-sterile plants, said method comprising:
   a) producing cytoplasmically male-sterile plants from a first parent plant line by:
      i) producing a plastid-transgenic parent plant from said parent plant line by stably transforming plastids in cells of said parent plant line with a plastid male sterility gene and regenerating a plastid-transgenic plant therefrom, said plastid male sterility gene being capable of regulation by a nuclear-encoded plastid-directed regulator polypeptide, said regulation in anther tissue causing disruption of formation of viable pollen;
      ii) producing a nuclear-transgenic parent plant from said parent plant line by stably transforming nuclei in cells of said parent plant line with a nuclear male sterility gene and regenerating a nuclear-transgenic plant therefrom, said nuclear male sterility gene comprising an anther-specific 5' regulatory nucleotide sequence operably linked to a coding nucleotide sequence that encodes said plastid-directed regulator polypeptide, which is capable of entering plastids and regulating said plastid male sterility gene; and
      iii) crossing said plastid-transgenic plant with said nuclear-transgenic plant to produce a plant in which said plastid-directed regulator polypeptide is anther-specifically produced, enters said transformed plastids of anther cells and regulates said plastid male sterility gene, said regulation causing disruption of formation of viable pollen, thereby producing said cytoplasmically male-sterile plants;
   b) producing male fertility restorer plants of a second parent plant line by stably transforming nuclei in cells of said second parent plant line with a restorer of male fertility gene and regenerating a plant therefrom, said restorer of male fertility gene encoding a restorer gene product capable of preventing said regulation of said plastid male sterility gene by said plastid-targeted regulator polypeptide, thereby enabling formation of viable pollen; and
   c) crossing said cytoplasmically male-sterile plants with said male fertility restorer plants to produce male-fertile hybrid seeds from said two parent plant lines.

20. A method according to claim 19, wherein:
   a) said plastid male sterility gene comprises a target nucleotide sequence having a site for activating gene expression and a site for preventing gene expression, said site for preventing gene expression being in a controlling position relative to said site for activating gene expression, said target nucleotide sequence being operably linked to a coding nucleotide sequence that encodes a gene product capable of disrupting said formation of viable pollen when expressed in plastids of anther cells;
   b) said nuclear male sterility gene encodes a plastid-directed activator polypeptide that enters plastids and specifically interacts with said site for activating gene expression, said interaction causing expression of said plastid male sterility gene; and
   c) said restorer of male fertility gene encodes a plastid-directed restorer polypeptide that enters plastids and specifically interacts with said site for preventing gene expression, said interaction preventing expression of said plastid male sterility gene.

21. A method according to claim 20, wherein said plastid-directed activator polypeptide comprises a transcriptional activator and said site for activation of gene expression comprises a regulatory region to which said transcriptional activator binds.

22. A method according to claim 21, wherein said transcriptional activator is a T7 RNA polymerase and said site for activation of gene expression comprises a T7 promoter.

23. A method according to claim 20, wherein said plastid-directed restorer polypeptide comprises a transcriptional repressor and said site for preventing gene expression comprises a regulatory region to which said transcriptional repressor binds.

24. A method according to claim 23, wherein said transcriptional repressor is a lac repressor and said site for preventing gene expression comprises at least one lac repressor binding site.

25. A method according to claim 19, wherein:
   a) said plastid male sterility gene comprises a first target nucleotide sequence for preventing gene expression, operably linked to an essential plastid gene, expression of which is necessary for plastid survival or function, said plastid male sterility gene being targeted to a plastid genome such that native forms of said essential plastid gene in transformed plastids are replaced with said plastid male sterility gene, prevention of expression of said plastid male sterility gene in plastids of anther cells being capable of disrupting said formation of viable pollen;

b) said nuclear male sterility gene comprises a second target nucleotide sequence for preventing gene expression, operably linked to a coding nucleotide sequence, which encodes a plastid-directed inactivator polypeptide that enters plastids and specifically interacts with said first target nucleotide sequence for preventing gene expression, said interaction preventing expression of said plastid male sterility gene; and c) said restorer of male fertility gene encodes a nuclear-directed restorer polypeptide that enters nuclei and specifically interacts with said second target nucleotide sequence for preventing gene expression, said interaction preventing expression of said nuclear male sterility gene.

26. A method according to claim 25, wherein said plastid-directed inactivator polypeptide comprises a transcriptional repressor and said first target nucleotide sequence comprises a regulatory region to which said transcriptional repressor binds.

27. A method according to claim 26, wherein said plastid-directed transcriptional repressor is a lac repressor and said first target nucleotide sequence comprises at least one lac repressor binding site.

28. A method according to claim 26, wherein said plastid-directed transcriptional repressor is a tet repressor and said first target nucleotide sequence comprises at least one tet repressor binding site.

29. A method according to claim 25, wherein said nuclear-directed restorer polypeptide comprises a transcriptional repressor and said second target nucleotide sequence comprises a regulatory region to which said transcriptional repressor binds.

30. A method according to claim 29, wherein said transcriptional repressor is a tet repressor and said second target nucleotide sequence comprises at least one tet repressor binding site.

31. A method according to claim 29, wherein said transcriptional repressor is a lac repressor and said second target nucleotide sequence comprises at least one lac repressor binding site.

32. A plant having transformed plastid genomes that include a stably integrated plastid male sterility gene, which is capable of regulation by a nuclear-encoded plastid-directed regulator polypeptide, said regulation in anther tissue causing disruption of formation of viable pollen.

33. A plant as claimed in claim 32, wherein said plastid male sterility gene comprises a target nucleotide sequence having a site for activating gene expression and a site for preventing gene expression, said site for preventing gene expression being in a controlling position relative to said site for activating gene expression, said target nucleotide sequence being operably linked to a coding nucleotide sequence that encodes a gene product capable of disrupting said formation of viable pollen when expressed in plastids of anther cells.

34. A plant as claimed in claim 33, wherein said target nucleotide sequence comprises a T7 promoter for activating gene expression and at least one lac repressor for preventing gene expression.

35. A plant as claimed in claim 32, wherein said plastid male sterility gene comprises a target nucleotide sequence for preventing gene expression, operably linked to an essential plastid gene, said plastid male sterility gene being targeted to a plastid genome such that native forms of said essential plastid gene in said transformed plastids are replaced with said plastid male sterility gene, prevention of expression of said plastid male sterility gene in plastids of anther cells being capable of disrupting said formation of viable pollen.

36. A plant as claimed in claim 35, wherein said target nucleotide sequence comprises at least one lac repressor binding site.

37. A plant having transformed nuclear genomes that include a stably integrated nuclear male sterility gene, which comprises a nucleotide sequence having an anther-specific 5' regulatory region operably linked to a nucleotide sequence that encodes a plastid-directed regulator polypeptide capable of entering plastids and regulating a plastid male sterility gene, said regulation resulting in disruption of formation of viable pollen.

38. A plant as claimed in claim 37, wherein said nuclear male sterility gene encodes a plastid-directed activator polypeptide that enters plastids and specifically interacts with a plastid male sterility gene comprising a target nucleotide sequence for activating gene expression, said interaction causing expression of said plastid male sterility gene, said expression resulting in disruption of formation of viable pollen.

39. A plant as claimed in claim 38, wherein said activator polypeptide is a T7 RNA polymerase.

40. A plant as claimed in claim 37, wherein said nuclear male sterility gene further comprises a target nucleotide sequence for preventing gene expression, operably linked to a nucleotide sequence encoding a plastid-directed inactivator polypeptide that enters plastids and specifically interacts with a plastid male sterility gene comprising another target nucleotide sequence for preventing gene expression, said interaction preventing expression of said plastid male sterility gene, said prevention of expression resulting in disruption of formation of viable pollen.

41. A plant as claimed in claim 40, wherein said inactivator polypeptide is a lac repressor.

42. A plant having transformed nuclear genomes that include a stably integrated restorer of male fertility gene that encodes a restorer gene product capable of preventing regulation of a regulatable plastid male sterility gene by a nuclear-encoded plastid-directed regulator polypeptide.

43. A plant as claimed in claim 42, wherein said restorer of male fertility gene encodes a plastid-directed restorer polypeptide that enters plastids and specifically interacts with a site for preventing gene expression, operably disposed within a plastid male sterility gene, said interaction preventing expression of said plastid male sterility gene.

44. A plant as claimed in claim 43, wherein said restorer polypeptide is selected from the group consisting of a lac repressor and a tet repressor.

45. A plant as claimed in claim 42, wherein said restorer of male fertility gene encodes a nucleus-directed restorer polypeptide that enters nuclei and specifically interacts with a target nucleotide sequence for preventing gene expression, operably disposed within a nuclear male sterility gene, said interaction preventing expression of said nuclear male sterility gene.

46. A plant as claimed in claim 45, wherein said restorer polypeptide is selected from the group consisting of a tet repressor and a lac repressor.

47. A cytoplasmically male-sterile plant having transformed plastid genomes that include a stably integrated plastid male sterility gene, which is capable of being regulated by a nuclear-encoded plastid-directed regulator polypeptide, and having nuclear genomes that include a stably integrated nuclear male sterility gene, which comprises a nucleotide sequence having an anther-specific 5' regulatory region operably linked to a nucleotide sequence that encodes a plastid-directed regulator polypeptide capable of entering plastids and regulating said plastid male sterility gene, said regulation resulting in disruption of formation of viable pollen.

48. A cytoplasmically male-sterile plant produced by a method which comprises:

a) providing a parent plant line;

b) producing a plastid-transgenic parent plant from said parent plant line by stably transforming plastids in cells of said parent plant line with a plastid male sterility gene and regenerating a plastid-transgenic plant therefrom, said plastid male sterility gene being capable of regulation by a nuclear-encoded plastid-directed regulator polypeptide, said regulation in anther tissue causing disruption of formation of viable pollen;

c) producing a nuclear-transgenic parent plant from said parent plant line by stably transforming nuclei in cells of said parent plant line with a nuclear male sterility gene and regenerating a nuclear-transgenic plant therefrom, said nuclear male sterility gene comprising an anther-specific 5' regulatory nucleotide sequence operably linked to a coding nucleotide sequence that encodes said plastid-directed regulator polypeptide, which is capable of entering plastids and regulating said plastid male sterility gene; and d) crossing said plastid-transgenic plant with said nuclear-transgenic plant to produce a plant in which said plastid-directed regulator polypeptide is anther-specifically produced, enters said transformed plastids of anther cells and regulates said plastid male sterility gene, said regulation causing disruption of formation of viable pollen.

49. Male-fertile hybrid seeds produced from two parent plant lines, one of which comprises cytoplasmically male-sterile plants, by a method which comprises:

a) producing cytoplasmically male-sterile plants from a first parent plant line by:

i) producing a plastid-transgenic parent plant from said parent plant line by stably transforming plastids in cells of said parent plant line with a plastid male sterility gene and regenerating a plastid-transgenic plant therefrom, said plastid male sterility gene being capable of regulation by a nuclear-encoded plastid-directed regulator polypeptide, said regulation in anther tissue causing disruption of formation of viable pollen;

ii) producing a nuclear-transgenic parent plant from said parent plant line by stably transforming nuclei in cells of said parent plant line with a nuclear male sterility gene and regenerating a nuclear-transgenic plant therefrom, said nuclear male sterility gene comprising an anther-specific 5' regulatory nucleotide sequence operably linked to a coding nucleotide sequence that encodes said plastid-directed regulator polypeptide, which is capable of entering plastids and regulating said plastid male sterility gene; and iii) crossing said plastid-transgenic plant with said nuclear-transgenic plant to produce a plant in which said plastid-directed regulator polypeptide is anther-specifically produced, enters said transformed plastids of anther cells and regulates said plastid male sterility gene, said regulation causing disruption of formation of viable pollen, thereby producing said cytoplasmically male-sterile plants;

b) producing male fertility restorer plants of a second parent plant line by stably transforming nuclei in cells of said second parent plant line with a restorer of male fertility gene that encodes a restorer gene product capable of preventing said regulation of said plastid male sterility gene by said plastid-targeted regulator polypeptide, thereby enabling formation of viable pollen, and regenerating a plant from said stably nuclear-transformed cell; and c) crossing said cytoplasmically male-sterile plants with said male fertility restorer plants to produce male-fertile hybrid seeds from said two parent plant lines.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
GAATTCGGGA  TCTCGATCCC  GCGAAATTAA  TACGACTCAC  TATAGGGGAA  TTGTGAGCGG      60
ATAACAATTC  CCCTCTAGCG  AGGCCTCGCT  AGAAATAATT  TTGTTTAACT  TTAAGAAGGA     120
GATATACCAT  GG                                                             132
```

( 2 ) INFORMATION FOR SEQ ID NO:2:

( i ) SEQUENCE CHARACTERISTICS:
        ( A ) LENGTH: 103 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

```
GAATTCGGGA  TCTCGATCCC  GCGAAATTAA  TACGACTCAC  TATAGGGGAA  TTGTGAGCGG      60
ATAACAATTC  CCCTCTAGTT  CAGTTGTAGG  GAGGGATCCA  TGG                        103
```

( 2 ) INFORMATION FOR SEQ ID NO:3:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

```
TCTAGAGCTG  AGCAATAACT  AGCATAACCC  CTTGGGGCCT  CTAAACGGGT  CTTGAGGGGT      60
TTTTTGCTGA  AAGGAGGAAC  TATATCCGGC  AAGCTT                                  96
```

( 2 ) INFORMATION FOR SEQ ID NO:4:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

| | | | | | |
|---|---|---|---|---|---|
| TCTAGAGAAA | TTCAATTAAG | GAAATAAATT | AAGGAAATAC | AAAAAGGGGG | GTAGTCATTT | 60 |
| GTATATAACT | TTGTATGACT | TTTCTCTTCT | ATTTTTTTGT | ATTTCCTCCC | TTTCCTTTTC | 120 |
| TATTTGTATT | TTTTTATCAT | TGCTTCCATT | GAATTAATTC | ATGCAAGCTC | CTCGCTAGAG | 180 |
| CTGAGCAATA | ACTAGCATAA | CCCCTTGGGG | CCTCTAAACG | GGTCTTGAGG | GGTTTTTGC | 240 |
| TGAAAGGAGG | AACTATATCC | GGCAAGCTT | | | | 269 |

(2) INFORMATION FOR SEQ ID NO:5:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

| | | | | | |
|---|---|---|---|---|---|
| ACAAGAACTA | ACAAAGTCAG | AAAAATGGCT | TCTATGATAT | CCTCTTCCGC | TGTGACAACA | 60 |
| GTCAGCCGTG | CTTCTAGGGT | GCAATCCGCG | GCAGTGGCTC | CATTCGGCGG | CCTGAAATCC | 120 |
| ATGACTGGAT | TCCCAGTGAA | GAAGGTCAAC | ACTGACATTA | CTTCCATTAC | AAGCAATGGT | 180 |
| GGAAGAGTAA | AGTGCATGCA | AACGATTAAC | ATCGCTAAGA | ACGACTTCTC | TGACATCGAA | 240 |

(2) INFORMATION FOR SEQ ID NO:6:

(i) SEQUENCE CHARACTERISTICS:
        (A) LENGTH: 72 amino acids
        (B) TYPE: amino acid
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:6:

```
Met Ala Ser Met Ile Ser Ser Ser Ala Val Thr Thr Val Ser Arg Ala
 1               5                  10                  15

Ser Arg Val Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Gln Thr Ile Asn Ile Ala
    50                  55                  60

Lys Asn Asp Phe Ser Asp Ile Glu
65                  70
```

(2) INFORMATION FOR SEQ ID NO:7:

(i) SEQUENCE CHARACTERISTICS:
        (A) LENGTH: 240 base pairs ( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

| ACAAGAACTA | ACAAAGTCAG | AAAAATGGCT | TCTATGATAT | CCTCTTCCGC | TGTGACAACA | 60 |
| GTCAGCCGTG | CTTCTAGGGT | GCAATCCGCG | GCAGTGGCTC | CATTCGGCGG | CCTGAAATCC | 120 |
| ATGACTGGAT | TCCCAGTGAA | GAAGGTCAAC | ACTGACATTA | CTTCCATTAC | AAGCAATGGT | 180 |
| GGAAGAGTAA | AGTGCATGCA | GGTGTGGCCT | CCCATGGTCA | CGATTAACAT | CGCTAAGAAC | 240 |

( 2 ) INFORMATION FOR SEQ ID NO:8:

( i ) SEQUENCE CHARACTERISTICS:
( A ) LENGTH: 72 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:8:

| Met | Ala | Ser | Met | Ile | Ser | Ser | Ser | Ala | Val | Thr | Thr | Val | Ser | Arg | Ala |
| 1 | | | | 5 | | | | | 10 | | | | | 15 | |
| Ser | Arg | Val | Gln | Ser | Ala | Ala | Val | Ala | Pro | Phe | Gly | Gly | Leu | Lys | Ser |
| | | | 20 | | | | 25 | | | | | 30 | | | |
| Met | Thr | Gly | Phe | Pro | Val | Lys | Lys | Val | Asn | Thr | Asp | Ile | Thr | Ser | Ile |
| | | 35 | | | | 40 | | | | | 45 | | | | |
| Thr | Ser | Asn | Gly | Gly | Arg | Val | Lys | Cys | Met | Gln | Val | Trp | Pro | Pro | Met |
| | 50 | | | | 55 | | | | | 60 | | | | | |
| Val | Thr | Ile | Asn | Ile | Ala | Lys | Asn | | | | | | | | |
| 65 | | | | 70 | | | | | | | | | | | |

( 2 ) INFORMATION FOR SEQ ID NO:9:

( i ) SEQUENCE CHARACTERISTICS:
( A ) LENGTH: 240 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

| ACAAGAACTA | ACAAAGTCAG | AAAAATGGCT | TCTATGATAT | CCTCTTCCGC | TGTGACAACA | 60 |
| GTCAGCCGTG | CTTCTAGGGT | GCAATCCGCG | GCAGTGGCTC | CATTCGGCGG | CCTGAAATCC | 120 |
| ATGACTGGAT | TCCCAGTGAA | GAAGGTCAAC | ACTGACATTA | CTTCCATTAC | AAGCAATGGT | 180 |
| GGAAGAGTAA | AGTGCATGCA | ACCAGTAACG | TTATACGATG | TCGCAGAGTA | TGCCGGTGTC | 240 |

( 2 ) INFORMATION FOR SEQ ID NO:10:

( i ) SEQUENCE CHARACTERISTICS:
    ( A ) LENGTH: 72 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

```
Met Ala Ser Met Ile Ser Ser Ser Ala Val Thr Thr Val Ser Arg Ala
1               5                   10                  15

Ser Arg Val Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Gly Pro Val Thr Leu Tyr
        50                  55                  60

Asp Val Ala Glu Tyr Ala Gly Val
65                  70
```

( 2 ) INFORMATION FOR SEQ ID NO:11:

( i ) SEQUENCE CHARACTERISTICS:
    ( A ) LENGTH: 240 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

```
ACAAGAACTA ACAAAGTCAG AAAAATGGCT TCTATGATAT CCTCTTCCGC TGTGACAACA     60
GTCAGCCGTG CTTCTAGGGT GCAATCCGCG GCAGTGGCTC CATTCGGCGG CCTGAAATCC    120
ATGACTGGAT TCCCAGTGAA GAAGGTCAAC ACTGACATTA CTTCCATTAC AAGCAATGGT    180
GGAAGAGTAA AGTGCATGCA GGTGTGGCCT CCCATGGGGA AACCAGTAAC GTTATACGAT    240
```

( 2 ) INFORMATION FOR SEQ ID NO:12:

( i ) SEQUENCE CHARACTERISTICS:
    ( A ) LENGTH: 72 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:12:

```
Met Ala Ser Met Ile Ser Ser Ser Ala Val Thr Thr Val Ser Arg Ala
1               5                   10                  15

Ser Arg Val Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45
```

```
        Thr  Ser  Asn  Gly  Gly  Arg  Val  Lys  Cys  Met  Gln  Val  Trp  Pro  Pro  Met
             50                  55                  60

Gly  Lys  Pro  Val  Thr  Leu  Tyr  Asp
        65                  70
```

( 2 ) INFORMATION FOR SEQ ID NO:13:

( i ) SEQUENCE CHARACTERISTICS:
        ( A ) LENGTH: 139 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

```
GCTCCCCCGC  CGTCGTTCAA  TGAGAATGGA  TAAGAGGCTC  GTGGGATTGA  CGTGAGGGGG      60
CAGGGATGGC  TATATTTCTG  GAATTGTGAG  CGGATAACAA  TTGGAGCGAA  CTCCGGGCGA     120
ATACGAAGCG  CTTGGATAC                                                     139
```

( 2 ) INFORMATION FOR SEQ ID NO:14:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

```
GCTCCCCCGC  CGTCGTTCAA  TGAGAATGGA  TAAGAGGCTC  GTGGGATTGA  CGAATTGTGA      60
GCGGATAACA  TATATTTCTG  GGAGCGAACT  CCGGGCGAAT  ACGAAGCGCT  TGGATAC        117
```

( 2 ) INFORMATION FOR SEQ ID NO:15:

( i ) SEQUENCE CHARACTERISTICS:
        ( A ) LENGTH: 161 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

```
GACAATTGAA  TCCGATTTTG  ACCATTATTT  TCATATCCGT  AATAGTGCGA  AAAGAAGGCC      60
CGGCTCCAAG  TTGTTCAAGA  ATAGTGGCGT  TGAGTTTCTC  GACCCTTTGA  CTTAGGATTA     120
GTGGAATTGT  GAGCGGATAA  CAATTCAGTT  CTATTTCTCG  A                         161
```

( 2 ) INFORMATION FOR SEQ ID NO:16:

( i ) SEQUENCE CHARACTERISTICS:
        ( A ) LENGTH: 171 base pairs
        ( B ) TYPE: nucleic acid
        ( C ) STRANDEDNESS: single -continued (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:16:

| GCTCCCCCGC | CGTCGTTCAA | TGAGAATGGA | TAAGAGGCTC | GTGGGATTGA | CGTGAGGGGG | 60 |
| CAGGGATGGC | TATATTTCTG | GAATTGTGAG | CGGATAACAA | TTGGAGCGAA | CTCCGGGCGA | 120 |
| ATTAGATCTA | GAAATAATTT | TGTTTAACTT | TAAGAAGGAG | ATATACCATG | G | 171 |

(2) INFORMATION FOR SEQ ID NO:17:

(i) SEQUENCE CHARACTERISTICS:
(A) LENGTH: 146 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:17:

| GCTCCCCCGC | CGTCGTTCAA | TGAGAATGGA | TAAGAGGCTC | GTGGGATTGA | CGTGAGGGGG | 60 |
| CAGGGATGGC | TATATTTCTG | GAATTGTGAG | CGGATAACAA | TTGGAGCGAA | CTCCGGGCGA | 120 |
| ATTCAGTTGT | AGGGAGGGAT | CCATGG | | | | 146 |